United States Patent
Yamada et al.

(10) Patent No.: US 10,861,903 B2
(45) Date of Patent: Dec. 8, 2020

(54) ORGANIC COMPOUND AND PHOTOELECTRIC CONVERSION ELEMENT

(71) Applicant: CANON KABUSHIKI KAISHA, Tokyo (JP)

(72) Inventors: Naoki Yamada, Inagi (JP); Yosuke Nishide, Kawasaki (JP); Hiroki Ohrui, Kawasaki (JP); Hironobu Iwawaki, Yokohama (JP); Hirokazu Miyashita, Ebina (JP); Jun Kamatani, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 22 days.

(21) Appl. No.: 16/051,724

(22) Filed: Aug. 1, 2018

(65) Prior Publication Data

US 2019/0043926 A1    Feb. 7, 2019

(30) Foreign Application Priority Data

Aug. 7, 2017 (JP) ................. 2017-152269

(51) Int. Cl.
| | |
|---|---|
| *C07D 495/04* | (2006.01) |
| *H01L 27/30* | (2006.01) |
| *H01L 51/00* | (2006.01) |
| *H04N 5/378* | (2011.01) |
| *H01L 51/44* | (2006.01) |
| *H01L 27/146* | (2006.01) |
| *H04N 5/374* | (2011.01) |
| *H01L 51/42* | (2006.01) |

(52) U.S. Cl.
CPC .......... *H01L 27/307* (2013.01); *C07D 495/04* (2013.01); *H01L 51/006* (2013.01); *H01L 51/0053* (2013.01); *H01L 51/0061* (2013.01); *H01L 51/0071* (2013.01); *H01L 51/441* (2013.01); *H04N 5/378* (2013.01); *H01L 27/14618* (2013.01); *H01L 27/14621* (2013.01); *H01L 27/14627* (2013.01); *H01L 51/0046* (2013.01); *H01L 51/4253* (2013.01); *H04N 5/374* (2013.01)

(58) Field of Classification Search
CPC .................................................. C07D 495/04
See application file for complete search history.

(56) References Cited

U.S. PATENT DOCUMENTS

| 6,583,557 | B2 | 6/2003 | Hashimoto et al. |
| 6,833,200 | B2 | 12/2004 | Senoo et al. |
| 2005/0025997 | A1 | 2/2005 | Senoo et al. |

FOREIGN PATENT DOCUMENTS

| JP | 2010-205815 A | 9/2010 |
| KR | 2015-136577 A | 12/2015 |
| WO | 2017/149958 A1 | 9/2017 |
| WO | 2018/016354 A1 | 1/2018 |

OTHER PUBLICATIONS

Eom, Y., et al. "New thieno[3,2-b][1]benzothiophene-based organic sensitizers containing π-extended thiophene spacers for efficient dye-sensitized solar cells." RSC Adv., (2015), vol. 5, pp. 80859-80870. (Year: 2015).*
Miyashita et al., U.S. Appl. No. 16/114,686, filed Aug. 28, 2018.
Nishide et al., U.S. Appl. No. 16/106,534, filed Aug. 21, 2018.
Nishide et al., U.S. Appl. No. 16/163,757, filed Oct. 18, 2018.
Yamada et al., U.S. Appl. No. 16/130,029, filed Sep. 13, 2018.
Non-final Office Action in U.S. Appl. No. 16/106,534 (dated May 7, 2020).
Yamada et al., U.S. Appl. No. 16/243,500, filed Jan. 9, 2019.

* cited by examiner

Primary Examiner — John S Kenyon
(74) Attorney, Agent, or Firm — Venable LLP

(57) ABSTRACT

Provided is an organic compound represented by the following general formula [1], the compound having an absorption peak in a long wavelength region of a visible light region:

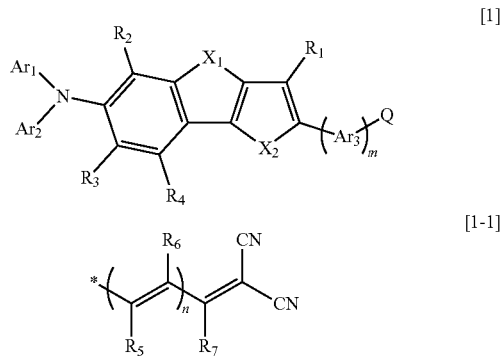

where $Ar_1$ and $Ar_2$ each represent an aryl group or the like, $Ar_3$ represents an arylene group or the like, m represents an integer of 0 to 3, $R_1$ to $R_4$ each represent a hydrogen atom or the like, $X_1$ and $X_2$ are each independently selected from oxygen and sulfur, Q represents, for example, a substituent represented by the general formula [1-1], $R_5$ to $R_7$ each represent a hydrogen atom or the like, and n represents an integer of 0 to 2.

14 Claims, 4 Drawing Sheets

ORGANIC COMPOUND AND PHOTOELECTRIC CONVERSION ELEMENT

BACKGROUND

Field of the Disclosure

The present disclosure relates to an organic compound, a photoelectric conversion element using the organic compound, and an imaging device and an imaging apparatus each using the photoelectric conversion element.

Description of the Related Art

A photoelectric conversion element is an element configured to receive light from the outside and to convert its energy into electrical energy. A solid imaging device having a sensor in which a plurality of photoelectric conversion elements are arrayed in a two-dimensional manner has been widely diffused by applying the foregoing characteristic. In recent years, the development of a photoelectric conversion element having an organic compound in its photoelectric conversion layer has been advanced, but in order that the element may be put into practical use, the element is susceptible to improvement in terms of, for example, conversion efficiency and durability.

The photoelectric conversion layer of the photoelectric conversion element is required to have the following characteristic. The layer has absorption in the entirety of a visible light region, and its sensitivity is high. To that end, it is preferred that a donor material have absorption in a red region (of from 600 nm to 750 nm), and its sensitivity be high.

In Japanese Patent Application Laid-Open No. 2010-205815 (hereinafter PTL 1), there is a description of Organic Compound a-1 having a thienobenzofuran structure, and there is a description of an organic light-emitting element using the compound. In Korean Patent Laid-Open Publication No. 2015-136577 (hereinafter PTL 2), there is a description of Organic Compound b-1 having a thienobenzothiophen structure, and there is a description of a dye-sensitized solar cell using the compound.

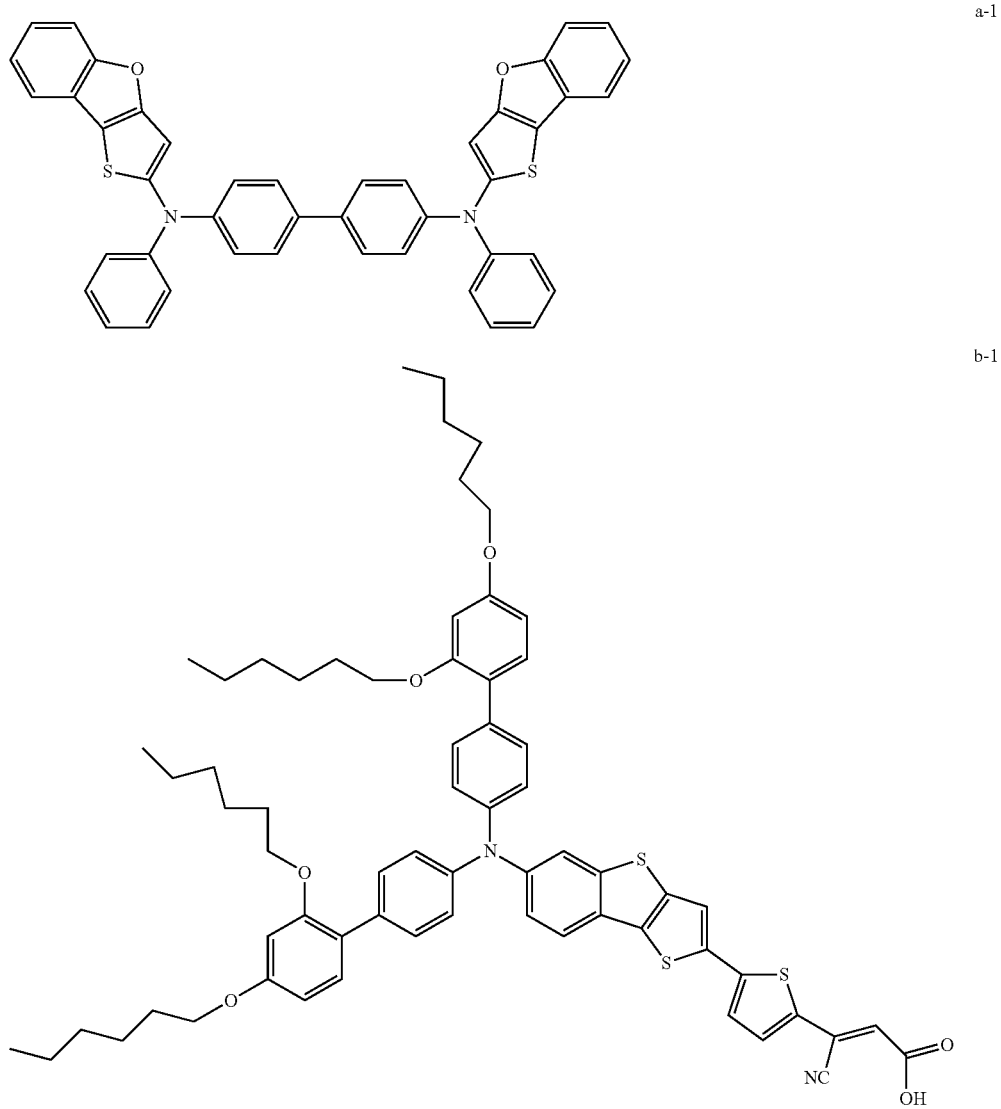

a-1 b-1

However, the organic compound described in PTL 1 has been a compound having a low absorptivity of light in a long wavelength region out of the visible light region. Meanwhile, a structure having a carboxyl group has been needed in the organic compound described in PTL 2 because the compound is used as a dye for a solar cell. The compound has been a compound having low thermal stability because the compound has a carboxyl group.

SUMMARY

The present disclosure has been made to solve the problems, and an object of the present disclosure is to provide an organic compound that has light absorption in a wide range of a visible light region and is excellent in thermal stability.

In view of the foregoing, according to one embodiment of the present disclosure, there is provided an organic compound, which is represented by the following general formula [1]:

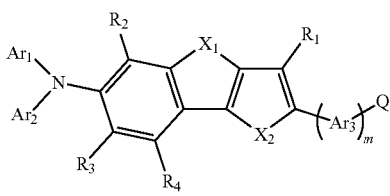

[1]

in the general formula [1], $Ar_1$ and $Ar_2$ are each independently selected from an aryl group and a heteroaryl group, the $Ar_1$ and the $Ar_2$ may each have a halogen atom, a cyano group, an alkyl group, an alkoxy group, an aryl group, or a heteroaryl group as a substituent, the substituent may further have a halogen atom, a cyano group, an alkyl group, or an alkoxy group as a substituent, the $Ar_1$ and the $Ar_2$ may be bonded to each other to form a ring, $Ar_3$'s are each independently selected from an arylene group and a heteroarylene group, and m represents an integer of 0 or more and 3 or less, and when the m represents 2 or 3, the $Ar_3$'s may be identical to or different from each other, $R_1$ to $R_4$ are each independently selected from a hydrogen atom, a halogen atom, a cyano group, an alkyl group, an alkoxy group, an aryl group, and a heteroaryl group, the alkyl group represented by any one of the $R_1$ to the $R_4$ may have a halogen atom as a substituent, and the aryl group and the heteroaryl group each represented by any one of the $R_1$ to the $R_4$ may each further have a halogen atom, a cyano group, an alkyl group, or an alkoxy group as a substituent, $X_1$ and $X_2$ are each independently selected from oxygen and sulfur, and Q represents a substituent independently selected from the following general formulae [1-1] and [1-2], and in each of the following general formulae [1-1] and [1-2], * represents a bonding position:

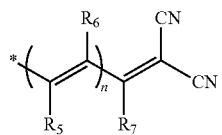

[1-1]

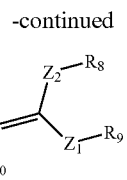

[1-2]

in the general formulae [1-1] and [1-2], $R_5$ to $R_{10}$ are each independently selected from a hydrogen atom, a halogen atom, a cyano group, an amino group, an amide group, an alkyl group, an alkoxy group, an alkenyl group, an alkynyl group, an aryl group, and a heteroaryl group, and the $R_7$ and the $R_5$ adjacent to the $R_7$ may be bonded to each other to form a ring, and the $R_8$ and the $R_9$ may be bonded to each other to form a ring, and the $R_5$ to the $R_{10}$ may each have a halogen atom, a cyano group, an alkyl group, an alkoxy group, an aryl group, or a heteroaryl group as a substituent, in the general formula [1-1], n represents an integer of 0 or more and 2 or less, and in the general formula [1-2], $Z_1$ and $Z_2$ are each independently selected from groups represented by the following formulae [1-3] to [1-5], and in each of the following formulae [1-3] to [1-5], * represents a bonding position.

[1-3]

[1-4]

[1-5]

Further features of the present invention will become apparent from the following description of exemplary embodiments with reference to the attached drawings.

DESCRIPTION OF THE EMBODIMENTS

Figure 1:
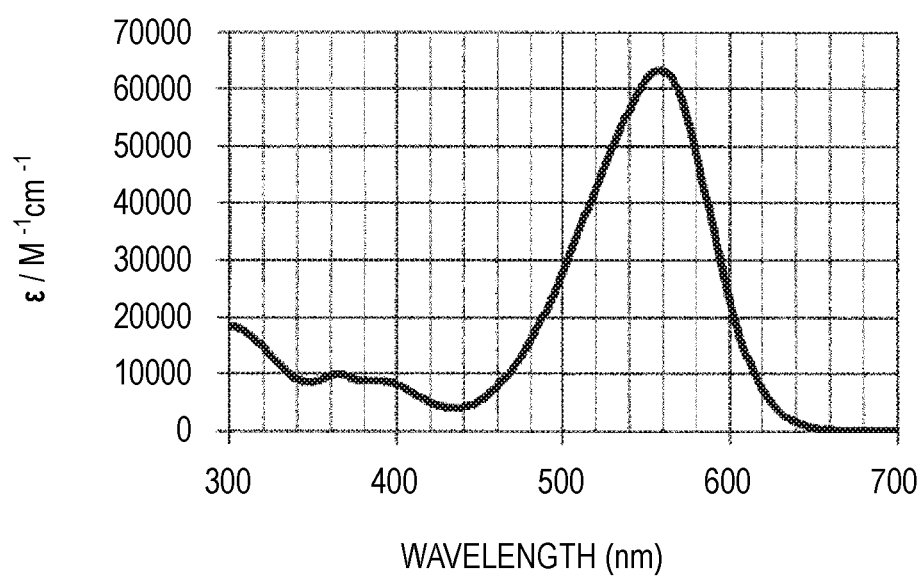
FIG. 1 is the absorption spectrum of Exemplified Compound B-1 according to an embodiment of the present disclosure in a chloroform dilute solution.

Preferred embodiments of the present invention will now be described in detail in accordance with the accompanying drawings.

[Organic Compound According to Embodiment of the Present Disclosure]

An organic compound according to an embodiment of the present disclosure is represented by the following general formula [1].

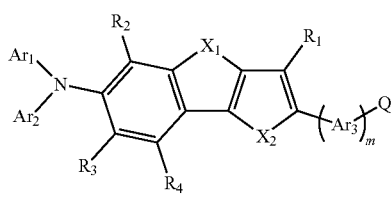

[1]

(1) $Ar_1$ and $Ar_2$

In the general formula [1], $Ar_1$ and $Ar_2$ are each independently selected from an aryl group and a heteroaryl group.

Examples of the aryl group include a phenyl group, a biphenyl group, a terphenyl group, a naphthyl group, a phenanthrenyl group, a chrysenyl group, a pyrenyl group, a fluorenyl group, and a fluoranthenyl group. Of those, a phenyl group, a biphenyl group, and a naphthyl group are particularly preferred.

Examples of the heteroaryl group include a pyridyl group, a pyrazyl group, a pyrimidyl group, a pyrididazoyl group, a triazyl group, a pyrrole group, a furanyl group, a thienyl group, an imidazole group, a pyrazole group, an oxazole group, a thiazole group, an imidazoline group, a thiazine group, a quinolinyl group, an isoquinolinyl group, an azaphenanthrenyl group, a phenanthronyl group, a benzothienyl group, a dibenzothienyl group, a benzofuranyl group, and a dibenzofuranyl group. Of those, a pyridyl group, a pyrazyl group, and a pyrimidyl group are preferred.

The $Ar_1$ and the $Ar_2$ may each have a halogen atom, a cyano group, an alkyl group, an alkoxy group, an aryl group, or a heteroaryl group as a substituent. The substituent may further have a halogen atom, a cyano group, an alkyl group, or an alkoxy group as a substituent. Specific examples of the aryl group and the heteroaryl group are as described above.

Examples of the halogen atom include a chlorine atom, a bromine atom, an iodine atom, and a fluorine atom. Of those, a fluorine atom is preferred.

Examples of the alkyl group include a methyl group, an ethyl group, a n-propyl group, an iso-propyl group, a n-butyl group, a tert-butyl group, a sec-butyl group, an octyl group, a 1-adamantyl group, and a 2-adamantyl group. Of those, alkyl groups each having 1 or more and 4 or less carbon atoms, such as a methyl group, an ethyl group, a n-propyl group, an iso-propyl group, a n-butyl group, a tert-butyl group, and a sec-butyl group, are preferred.

Examples of the alkoxy group include a methoxy group, an ethoxy group, a n-propoxy group, an iso-propoxy group, a n-butoxy group, a tert-butoxy group, and a sec-butoxy group. Of those, alkoxy groups each having 1 or more and 10 or less carbon atoms, specifically having 1 or more and 4 or less carbon atoms, such as a methoxy group, an ethoxy group, a n-propoxy group, an iso-propoxy group, a n-butoxy group, a tert-butoxy group, a sec-butoxy group, an octyloxy group, a 1-adamantyloxy group, and a 2-adamantyloxy group, are preferred.

The $Ar_1$ and the $Ar_2$ may be bonded to each other to form a ring. At this time, the $Ar_1$ and the $Ar_2$ may be bonded to each other through a heteroatom, such as nitrogen, oxygen, or sulfur. The ring to be formed, which is not particularly limited, is preferably a five-membered ring, a six-membered ring, or a seven-membered ring. The ring to be formed may be an aromatic ring, may be an aliphatic ring, or may be a ring partially having a double bond. In addition, the formed ring may contain a heteroatom, such as nitrogen, oxygen, or sulfur.

(2) $Ar_3$ and m

In the general formula [1], $Ar_3$'s are each independently selected from an arylene group and a heteroarylene group, and m represents an integer of 0 or more and 3 or less, preferably 0, and when the m represents 2 or 3, the $Ar_3$'s may be identical to or different from each other. When the m represents 0, the site represents a direct bond.

Examples of the arylene group include a phenylene group, a biphenylene group, a naphthylene group, a phenanthrylene group, and a fluorenylene group.

Examples of the heteroarylene group include a pyridylene group, a quinolylene group, an isoquinolylene group, a thienylene group, a furanylene group, a benzothienylene group, and a benzofuranylene group.

(3) $R_1$ to $R_4$

In the general formula [1], $R_1$ to $R_4$ are each independently selected from a hydrogen atom, a halogen atom, a cyano group, an alkyl group, an alkoxy group, an aryl group, and a heteroaryl group. Specific examples of the halogen atom, the alkyl group, the alkoxy group, the aryl group, and the heteroaryl group are as listed for the $Ar_1$ and the $Ar_2$. The alkyl group may have a halogen atom as a substituent. The aryl group and the heteroaryl group may each have a halogen atom, a cyano group, an alkyl group, or an alkoxy group as a substituent. Specific examples of the halogen atom, the alkyl group, and the alkoxy group are as listed for the $Ar_1$ and the $Ar_2$.

(4) $X_1$ and $X_2$

In the general formula [1], $X_1$ and $X_2$ are each independently selected from oxygen and sulfur. A case in which the $X_1$ represents oxygen and the $X_2$ represents sulfur is preferred because the strain of a ring structure containing the $X_1$ and the $X_2$ becomes smaller, and hence the stability of the compound is improved.

(5) Q

In the general formula [1], Q represents an electron-withdrawing substituent independently selected from the following general formulae [1-1] and [1-2]. In each of the general formulae [1-1] and [1-2], * represents a bonding position.

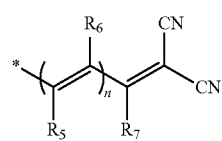

[1-1]

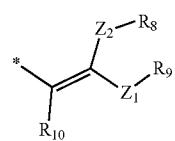

[1-2]

In the general formulae [1-1] and [1-2], $R_5$ to $R_{10}$ are each independently selected from a hydrogen atom, a halogen atom, a cyano group, an amino group, an amide group, an alkyl group, an alkoxy group, an alkenyl group, an alkynyl group, an aryl group, and a heteroaryl group.

Specific examples of the halogen atom, the alkyl group, the alkoxy group, the aryl group, and the heteroaryl group are as listed for the $Ar_1$ and the $Ar_2$.

The amino group may be, for example, an amino group in which a hydrogen atom is substituted, and examples thereof include substituted amino groups having substituents, such as an alkyl group, an aryl group having 6 or more and 18 or less carbon atoms, and a heteroaryl group having 3 or more and 17 or less carbon atoms.

The amide group may be, for example, an amide group in which a hydrogen atom is substituted, and examples thereof include substituted amide groups having substituents, such as an alkyl group, an aryl group having 6 or more and 18 or less carbon atoms, and a heteroaryl group having 3 or more and 17 or less carbon atoms.

The alkenyl group may be, for example, an alkenyl group in which a hydrogen atom is substituted, and examples thereof include substituted alkenyl groups having substituents, such as a halogen atom, an alkyl group, an alkoxy group, an aryl group having 6 or more and 18 or less carbon atoms, and a heteroaryl group having 3 or more and 17 or less carbon atoms.

The alkynyl group may be, for example, an alkynyl group in which a hydrogen atom is substituted, and examples thereof include substituted alkynyl groups having substituents, such as a halogen atom, an alkyl group, an alkoxy group, an aryl group having 6 or more and 18 or less carbon atoms, and a heteroaryl group having 3 or more and 17 or less carbon atoms.

The $R_5$ to the $R_{10}$ may each have a halogen atom, a cyano group, an alkyl group, an alkoxy group, an aryl group, or a heteroaryl group as a substituent.

Specific examples of the halogen atom, the alkyl group, the alkoxy group, the aryl group, and the heteroaryl group are as listed for the $Ar_1$ and the $Ar_2$.

In addition, the $R_7$ and the $R_5$ adjacent to the $R_7$, or the $R_8$ and the $R_9$ may be bonded to each other to form a ring. At this time, the $R_7$ and the $R_5$ adjacent to the $R_7$, or the $R_8$ and the $R_9$ may be bonded to each other through a heteroatom, such as nitrogen, oxygen, or sulfur. The ring to be formed, which is not particularly limited, is preferably a five-membered ring, a six-membered ring, or a seven-membered ring. The ring to be formed may be an aromatic ring, may be an aliphatic ring, or may be a ring partially having a double bond. In addition, the formed ring may contain a heteroatom, such as nitrogen, oxygen, or sulfur.

In the general formula [1-1], n represents an integer of 0 or more and 2 or less.

In the general formula [1-2], $Z_1$ and $Z_2$ are each independently selected from groups represented by the following formulae [1-3] to [1-5], and at least one of the $Z_1$ or the $Z_2$ preferably represents a group represented by the formula [1-3] or the formula [1-5]. In each of the following formulae [1-3] to [1-5], * represents a bonding position.

[1-3]

[1-4]

[1-5]

(6) Preferred Compound

A case in which the Q is represented by the general formula [1-2], and the $R_8$ and the $R_9$ are bonded to each other to form a ring is preferred because the lengthening of the absorption wavelength of the organic compound and an improvement in thermal stability thereof, in particular, an increase in melting point thereof are achieved. Examples of the structure of the ring to be formed are represented by the following general formulae [2-1] to [2-9]. * represents a bonding position, and a chemical formula on the left side and any one of the chemical formulae represented by the general formulae [2-1] to [2-9] are bonded to each other at the position represented by *.

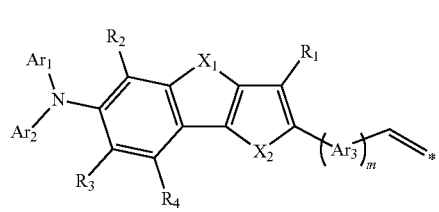

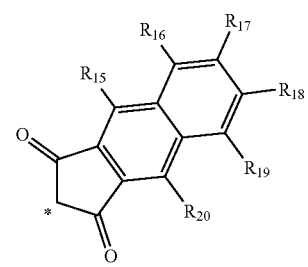

[2-1]

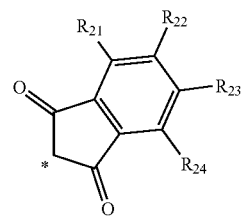

[2-2]

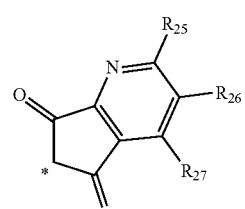

[2-3]

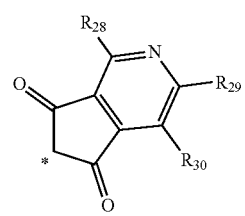

[2-4]

[2-5]

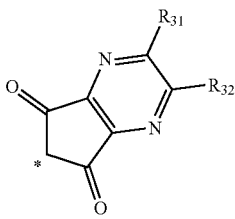

[2-6]

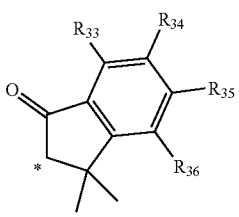

[2-7]

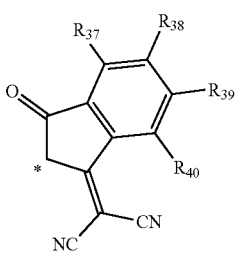

[2-8]

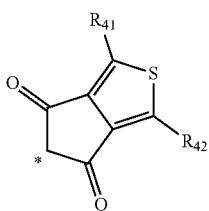

[2-9]

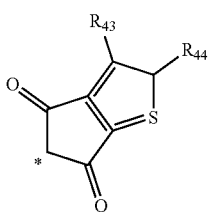

In the general formulae [2-1] to [2-9], $R_{15}$ to $R_{44}$ are each independently selected from a hydrogen atom, a halogen atom, a cyano group, an alkyl group, an alkoxy group, an aryl group, and a heteroaryl group.

In addition, a case in which the Q is represented by the general formula [1-2], and the $Z_1$ and the $Z_2$ each represent a carbonyl group is preferred because the thermal stability of the organic compound, in particular, the melting point thereof is high, and an organic compound represented by the following general formula [2] is more preferred.

[2]

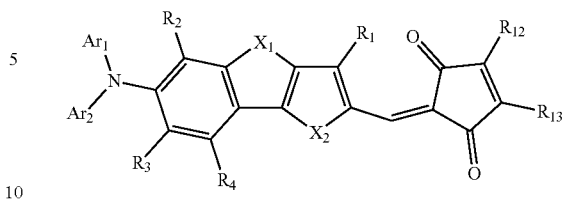

In the general formula [2], $R_{12}$ and $R_{13}$ are each independently selected from a hydrogen atom, a halogen atom, a cyano group, an amino group, an amide group, an alkyl group, an alkoxy group, an alkenyl group, an alkynyl group, an aryl group, and a heteroaryl group, and the $R_{12}$ and the $R_{13}$ may each have a halogen atom, a cyano group, an alkyl group, an alkoxy group, an aryl group, or a heteroaryl group as a substituent. Specific examples of the $R_{12}$ and the $R_{13}$ are as listed for the $R_5$ to the $R_{10}$.

The $R_{12}$ and the $R_{13}$ may be bonded to each other to form a ring as in the $R_8$ and the $R_9$ in the general formula [1-2]. At this time, the $R_{12}$ and the $R_{13}$ may be bonded to each other through a heteroatom, such as nitrogen, oxygen, or sulfur. The ring to be formed, which is not particularly limited, is preferably a five-membered ring, a six-membered ring, or a seven-membered ring. The ring to be formed may be an aromatic ring, may be an aliphatic ring, or may be a ring partially having a double bond. In addition, the formed ring may contain a heteroatom, such as nitrogen, oxygen, or sulfur. Examples of the ring formed by the bonding of the $R_{12}$ and the $R_{13}$ to each other include a benzene ring, a naphthalene ring, a pyridine ring, a pyrimidine ring, a pyrazine ring, a pyridazine ring, a quinoline ring, an isoquinoline ring, a quinoxaline ring, a thiophene ring, a benzothiophene ring, a furan ring, and a benzofuran ring.

A case in which the Q is represented by the general formula [1-1] and the n represents 0 is preferred because the molecular weight of the organic compound becomes smaller and the sublimation temperature thereof reduces, and an organic compound represented by the following general formula [3] is more preferred.

[3]

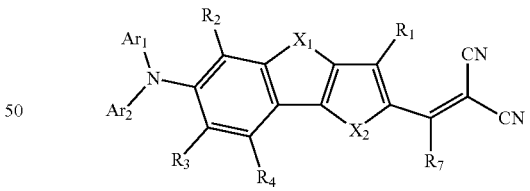

[Features of Organic Compound According to Embodiment of the Present Disclosure]

(1) Panchromatic Performance

Panchromatic performance refers to such an ability that the organic compound has high absorption sensitivity in the entirety of a visible light region.

When the organic compound is used as a photoelectric conversion film to capture light in the visible light region as a charge signal, the compound is preferably capable of absorbing light in the entirety of the visible light region of from 380 nm to 750 nm. In particular, its absorption sensitivity in a red region (of from 600 nm to 750 nm) is preferably high. Specifically, an absorption edge (position at which an absorption spectrum rises up) at longer wavelengths of the compound in a thin film state is preferably present in the red region (of 600 nm or more). In addition, an absorption edge at longer wavelengths of the compound in a chloroform dilute solution (solution having a concentration of less than $5\times10^{-5}$ mol/L) is preferably present at 580 nm or more, and is more preferably present at 600 nm or more. In that case, the maximum absorption wavelength of the chloroform dilute solution is preferably present at from 515 nm to 615 nm. In addition, the molar extinction coefficient of the compound at the maximum absorption wavelength is preferably high.

The organic compound according to the embodiment of the present disclosure has the following features: the maximum absorption wavelength of a chloroform dilute solution of the compound is present at from 515 nm to 615 nm, and its molar extinction coefficient at the maximum absorption wavelength is high. In addition, when an n-type semiconductor, such as a fullerene analog, is used as an electron acceptor, absorption sensitivity particularly at shorter wavelengths ranging from 380 nm to 500 nm in addition to the absorption region of the organic compound according to the embodiment of the present disclosure can be further improved. Thus, the panchromatic performance is further improved.

As can be seen from the foregoing, when the organic compound according to the embodiment of the present disclosure is used in a photoelectric conversion element, the organic compound according to the embodiment of the present disclosure alone can be responsible for light absorption in the entirety of the visible light region. When the number of compounds responsible for the light absorption is one, the orientation and aggregation state of the molecules of the compound can be easily controlled, and hence the occurrence of a trap level can be suppressed. In addition, when the light absorption sensitivity of the organic compound is high, the film thickness of the compound can be reduced, and the driving voltage of the element is small.

In contrast, when a compound having weak absorption sensitivity in the red region like a comparative compound is used in the element, several kinds of compounds need to be mixed, or the film thickness needs to be increased in order that the compound may be caused to absorb light. When the film thickness is increased, the driving voltage increases and the risk of the occurrence of a trap level becomes higher. When the trap level occurs, an increase in driving voltage due to a reduction in conversion efficiency of the element occurs. Therefore, a case in which the thickness is increased is not preferred because the driving voltage of the element is high.

(2) Photoelectric Conversion Characteristic

The organic compound according to the embodiment of the present disclosure has a feature of having an amino group on its basic skeleton, such as a thienobenzofuran skeleton. Accordingly, the compound has a high electron-donating property, and hence when the compound is used in a photoelectric conversion layer together with an n-type semiconductor, such as a fullerene analog, the compound functions as an electron donor to perform satisfactory photoelectric conversion. In addition, the compound has high redox stability and hence the repeated use durability of a photoelectric conversion element having the layer is high.

(3) Thermal Stability

The organic compound according to the embodiment of the present disclosure has high thermal stability. The compound has a high decomposition temperature because the compound is free of a substituent having a low decomposition temperature. In addition, the sublimation purification of the compound can be simply performed because the compound has so low a sublimation starting temperature as not to decompose. Accordingly, the purity of the organic compound according to the embodiment of the present disclosure can be easily improved by its sublimation purification.

By virtue of the foregoing features, even when an element is produced from the organic compound according to the embodiment of the present disclosure by using a vacuum deposition process, the element can be stably formed without the decomposition of the compound.

[Comparison Between Exemplified Compound B-1 According to Embodiment of the Present Disclosure and Comparative Compound a-1]

Exemplified Compound B-1 of the organic compound according to the embodiment of the present disclosure is represented by the following structural formula.

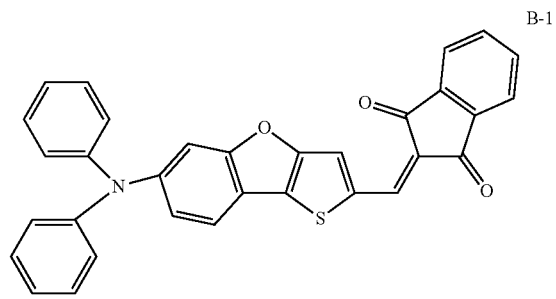 [SMILES: O=C1C(=Cc2cc3oc4cc(N(c5ccccc5)c5ccccc5)ccc4c3s2)C(=O)c2ccccc21]

B-1

Comparative Compound a-1 is represented by the following structural formula.

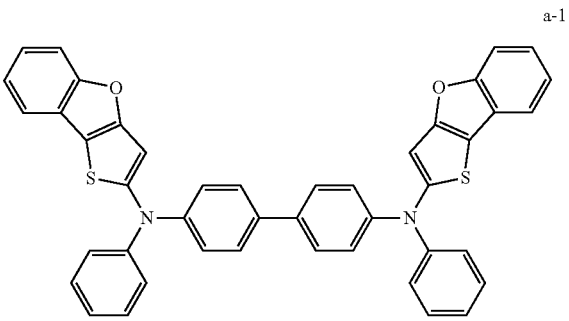 [SMILES: c1ccc(N(c2ccc(-c3ccc(N(c4ccccc4)c4cc5oc6ccccc6c5s4)cc3)cc2)c2cc3oc4ccccc4c3s2)cc1]

a-1

Exemplified Compound B-1 according to the embodiment of the present disclosure and Comparative Compound a-1 were compared to each other in terms of the range of a visible light absorption region.

Exemplified Compound B-1 according to the embodiment of the present disclosure has absorption in the entirety of the visible light region. The absorption spectrum of Exemplified Compound B-1 according to the embodiment of the present disclosure in a chloroform dilute solution ($3\times10^{-5}$ mol/L) is shown in FIG. 1. The absorption spectrum of Exemplified Compound B-1 according to the embodiment of the present disclosure has an end portion at a wavelength of 650 nm, and has a maximum absorption peak wavelength of 558 nm. That is, the compound has light absorption in the red region, and is hence preferred as a compound to be used in a photoelectric conversion element.

Calculated values for the absorption wavelengths of the organic compound according to the embodiment of the present disclosure and Comparative Compound a-1 are shown in Table 1.

TABLE 1

| Compound | Structure | Calculated value for absorption wavelength (nm) |
| --- | --- | --- |
| Present Disclosure Compound 1 | 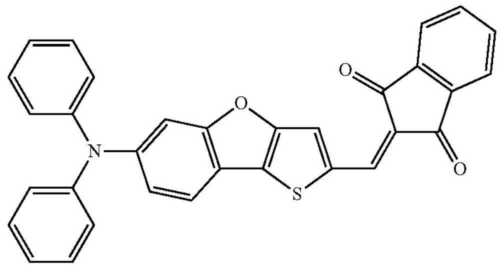 [SMILES: O=C1C(=Cc2cc3oc4cc(N(c5ccccc5)c5ccccc5)ccc4c3s2)C(=O)c2ccccc21] | 531 |
| Present Disclosure Compound 2 | 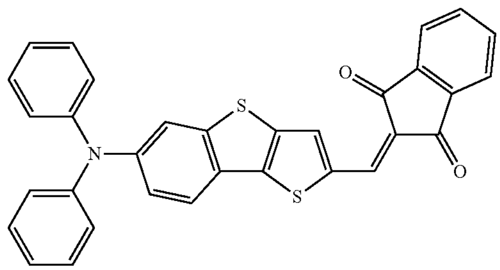 [SMILES: O=C1C(=Cc2cc3sc4cc(N(c5ccccc5)c5ccccc5)ccc4c3s2)C(=O)c2ccccc21] | 531 |
| Present Disclosure Compound 3 | 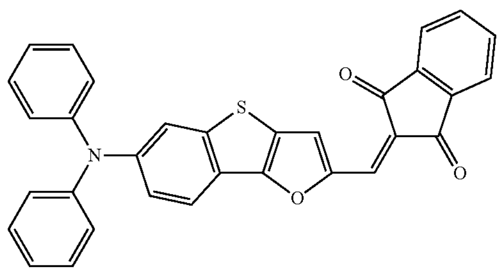 [SMILES: O=C1C(=Cc2cc3sc4cc(N(c5ccccc5)c5ccccc5)ccc4c3o2)C(=O)c2ccccc21] | 518 |
| Present Disclosure Compound 4 | 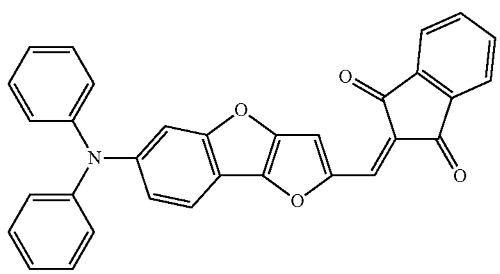 [SMILES: O=C1C(=Cc2cc3oc4cc(N(c5ccccc5)c5ccccc5)ccc4c3o2)C(=O)c2ccccc21] | 514 |
| Comparative Compound a-1 | 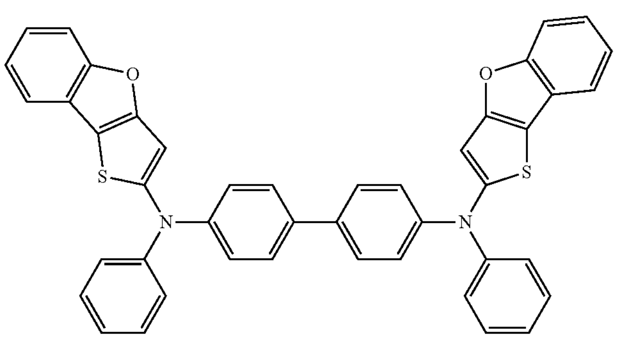 [SMILES: c1ccc(N(c2ccc(-c3ccc(N(c4ccccc4)c4cc5oc6ccccc6c5s4)cc3)cc2)c2cc3oc4ccccc4c3s2)cc1] | 390 |

As shown in Table 1, the calculated values for the absorption wavelengths of Present Disclosure Compounds 1 to 4 each serving as the organic compound according to the embodiment of the present disclosure are from 531 nm to 514 nm. In addition, Present Disclosure Compound 1 is Exemplified Compound B-1, and as described above, the absorption spectrum of Exemplified Compound B-1 has the end portion at 650 nm and has a maximum absorption peak wavelength of 558 nm. It can be said from the foregoing that Present Disclosure Compounds 1 to 4 have absorption peaks at wavelengths around from 558 nm to 541 nm, and their absorption spectra have end portions around from 650 nm to 633 nm.

It can be said that the organic compound according to the embodiment of the present disclosure has an absorption peak at longer wavelengths than Comparative Compound a-1 does and has absorption in the red region (of from 600 nm to 750 nm), and its sensitivity is high.

Density functional theory (DFT) widely used at present was used as a calculation approach for molecular orbital calculation. B3LYP was used as a functional and 6-31G* was used as a basis function. The molecular orbital calculation was performed through use of Gaussian 09 widely used at present (Gaussian 09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford Conn., 2010.).

The difference results from the presence or absence of an electron-withdrawing group. The absorption spectrum of Exemplified Compound B-1 according to the embodiment of the present disclosure covers a long wavelength range because the compound has a group having a strong electron-withdrawing property as a substituent on its thiophene side. In other words, the thienobenzofuran main skeleton of Exemplified Compound B-1 according to the embodiment of the present disclosure has bonded thereto a group having an amino group, which is electron-donating, and a carbonyl group, which is electron-withdrawing, and hence the absorption wavelength of the thienobenzofuran main skeleton can be largely lengthened.

Meanwhile, Comparative Compound a-1 is free of any electron-withdrawing group. Accordingly, its absorption spectrum covers a short wavelength range, and no absorption is present in the red region (of from 600 nm to 750 nm). The compound is designed for a transport material for an organic light-emitting element, and is hence designed so that its absorption wavelength may be so short as not to include the visible light region.

[Comparison Between Exemplified Compound B-1 According to Embodiment of the Present Disclosure and Comparative Compound b-1]

Comparative Compound b-1 is represented by the following structural formula.

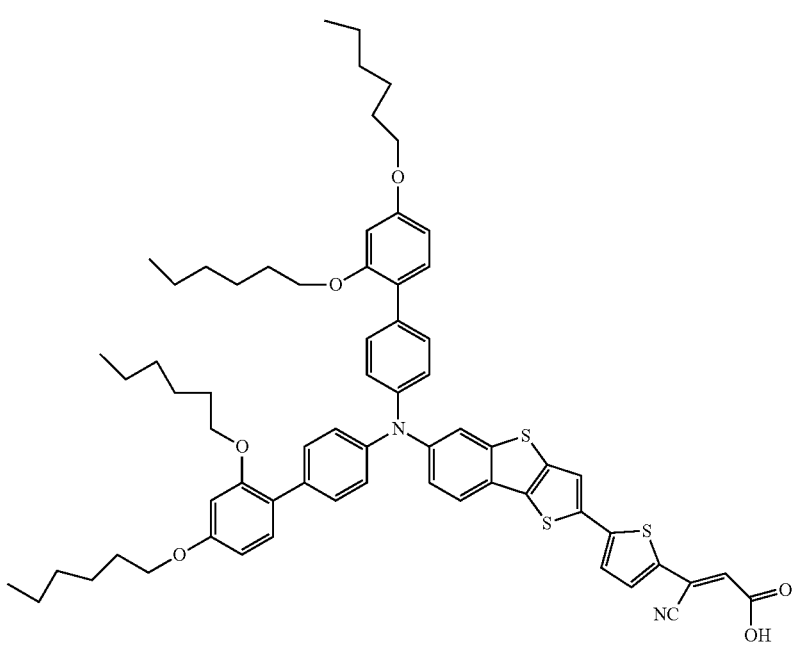

b-1

The sublimation purification of the organic compound according to the embodiment of the present disclosure can be simply performed because its thermal stability is high. The decomposition temperature of Exemplified Compound B-1 according to the embodiment of the present disclosure was as high as 300° C. or more, and hence its sublimation purification was able to be stably performed. The purity of the organic compound according to the embodiment of the present disclosure can be easily improved by its sublimation purification.

In contrast, Comparative Compound b-1 has a carboxyl group, and hence has a low decomposition temperature and low thermal stability. Accordingly, the compound is unsuitable for sublimation purification and vacuum deposition. Comparative Compound b-1 is a compound to be used in a dye-sensitized solar cell, and has a carboxyl group because the compound needs to be used as a photoelectric conversion compound to chemically modify a metal oxide, such as titanium oxide. A structure having a Bronsted acid serving as a proton donor, such as a carboxyl group, is used in a photoelectric conversion compound for a dye-sensitized solar cell.

An element can be stably formed from an organic compound having high thermal stability even when the element is produced by using a vacuum deposition process. In contrast, the vacuum deposition process cannot be used for a compound having low thermal stability because the compound causes thermal decomposition. When a compound has a structure like a carboxyl group, an intermolecular hydrogen bond occurs to dimerize the compound, and hence its molecular weight increases. In addition, carboxyl groups each having high reactivity are bonded to each other to cause the thermal decomposition of the compound.

[Examples of Organic Compound According to Embodiment of the Present Disclosure]

Specific structural formulae of the organic compound according to the embodiment of the present disclosure are listed in the following groups ranging from a group A to a group H. However, the present disclosure is not limited to these specific examples.

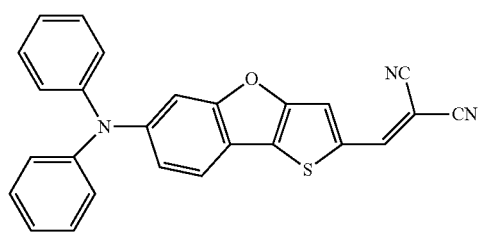

A-1

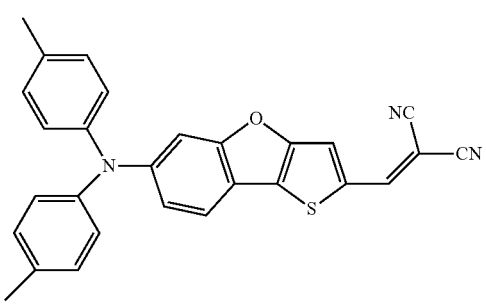

A-2

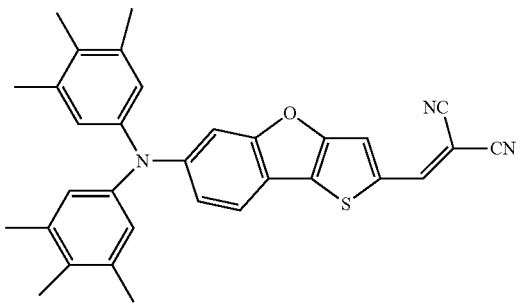

A-3

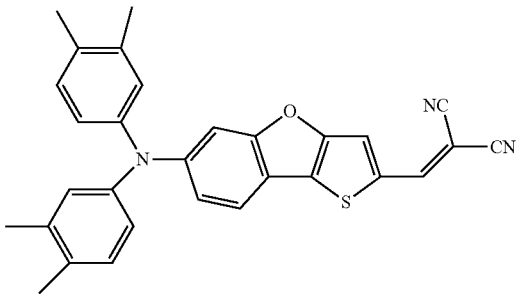

A-4

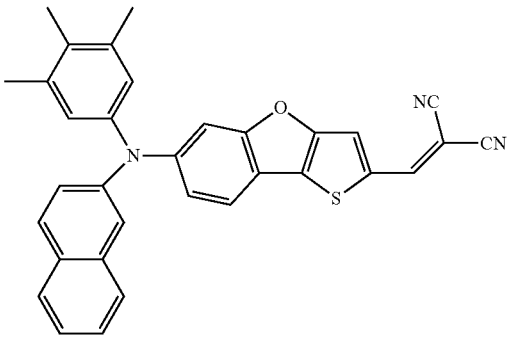

A-5

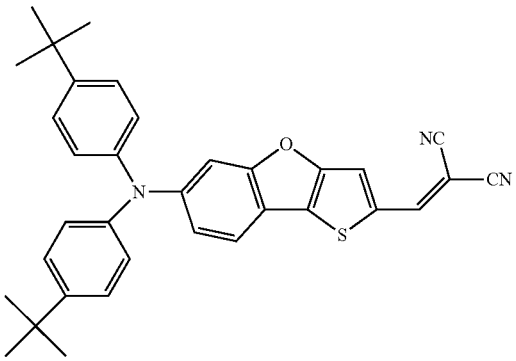

A-6

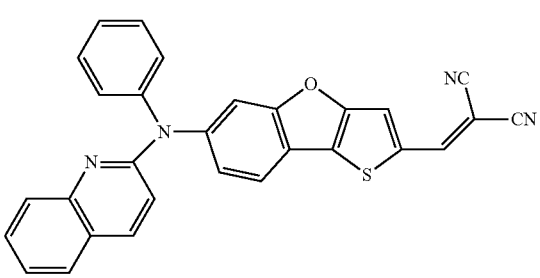

A-7

A-8
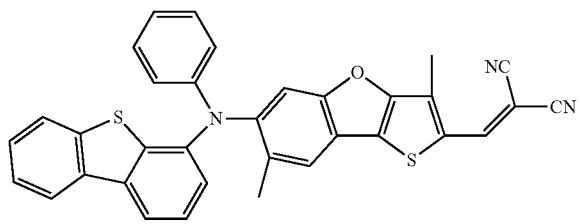
A-9
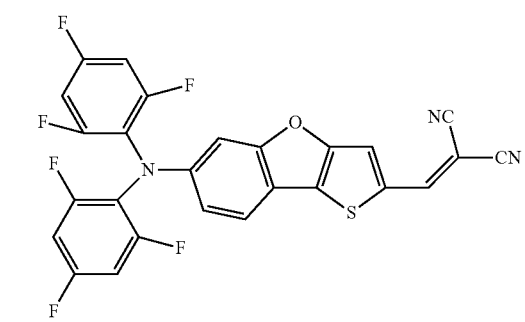
A-10
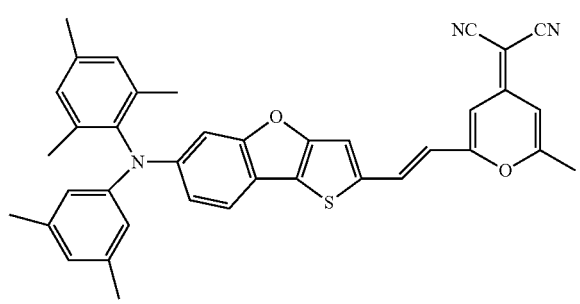
A-11
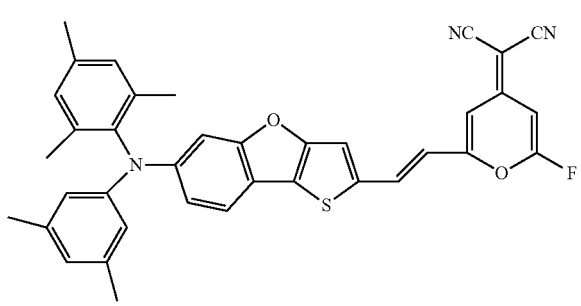
A-12
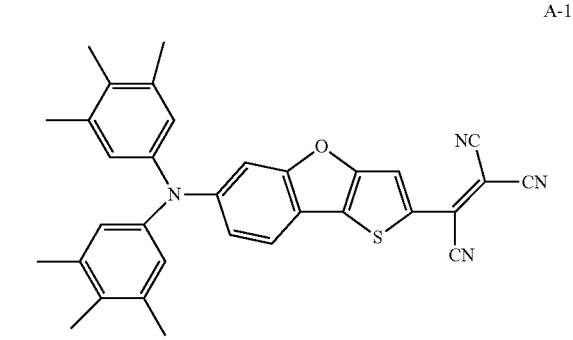
A-13
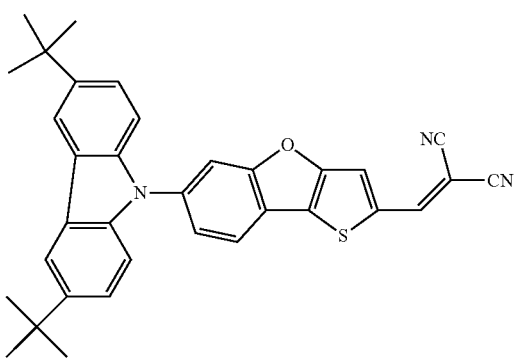
A-14
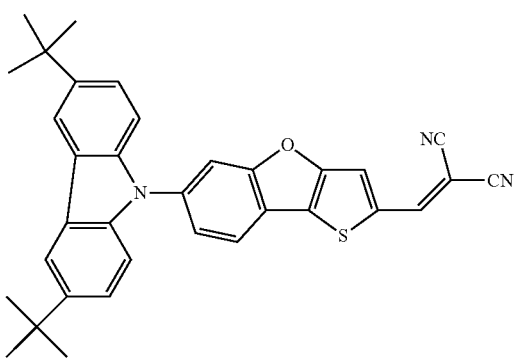
A-15
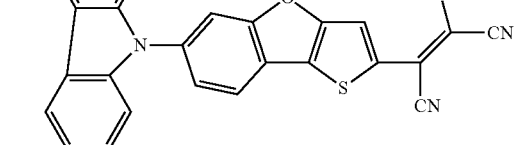
A-16
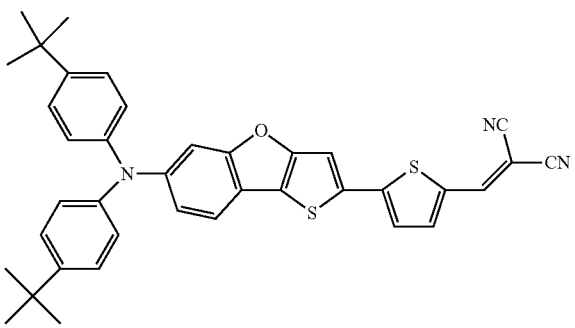

A-17 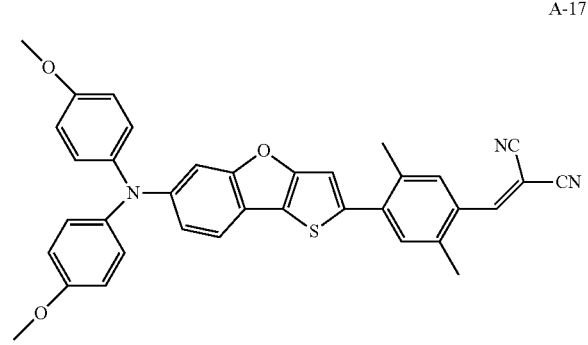
A-18 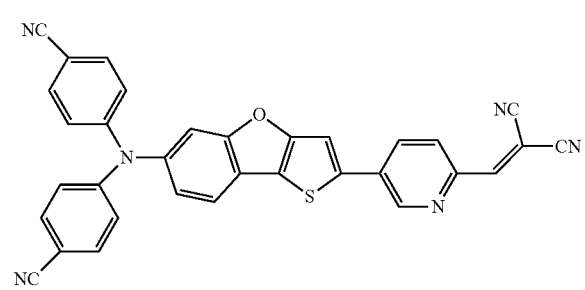
A-19 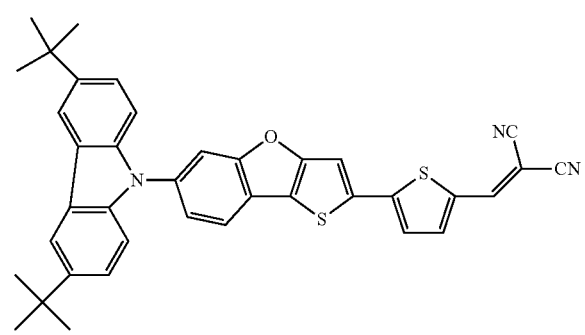
A-20 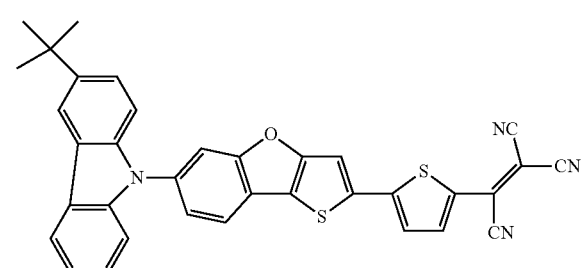
A-21 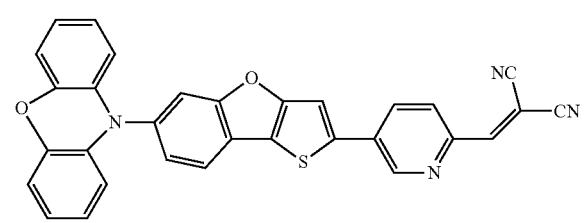
B-1 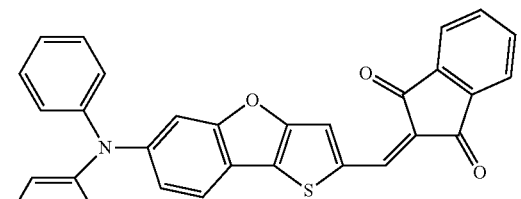
B-2 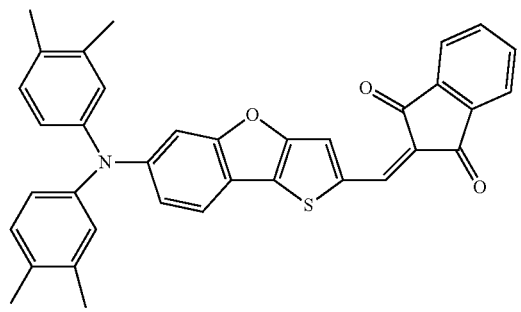
B-3 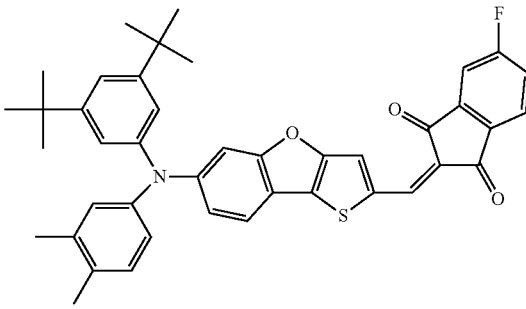
B-4 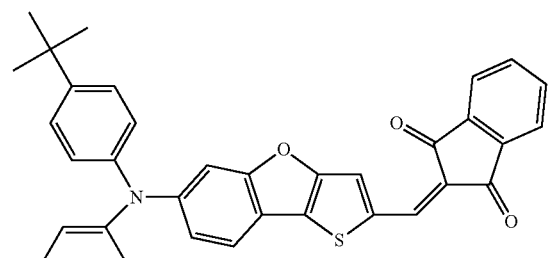
B-5 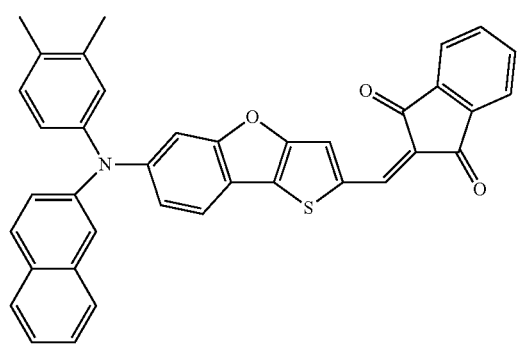

-continued
B-6
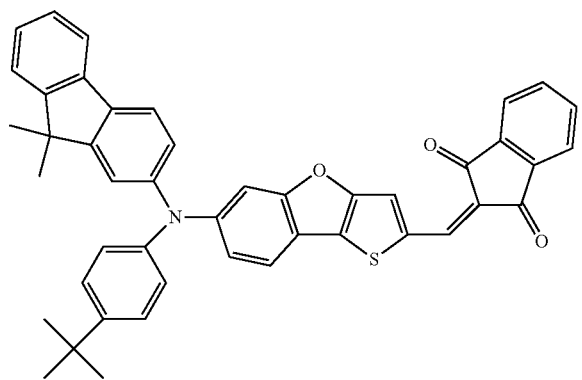
B-7
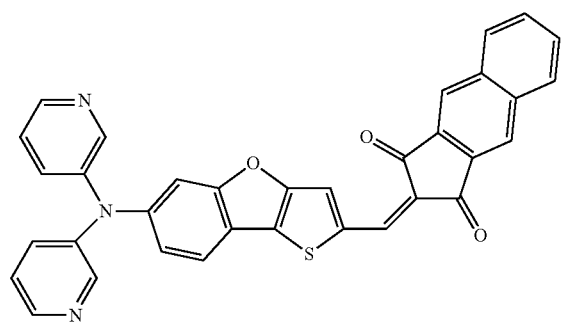
B-8
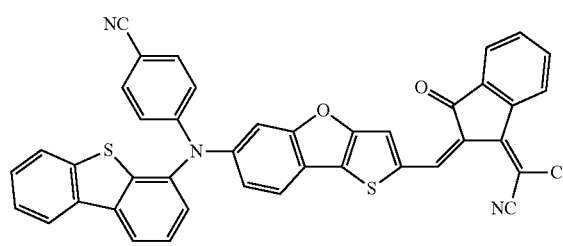
B-9
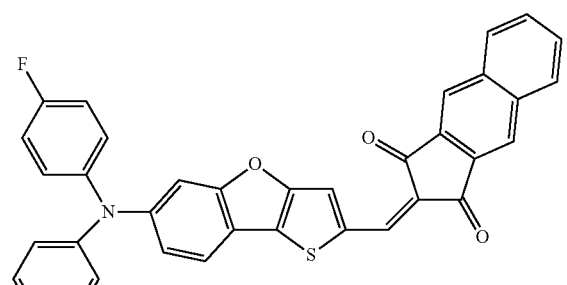
-continued
B-10
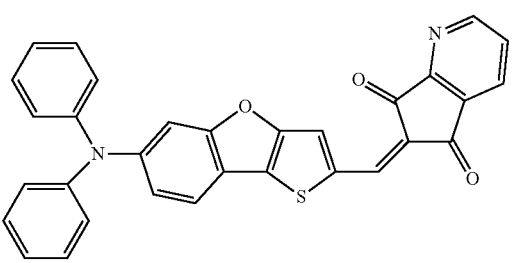
B-11
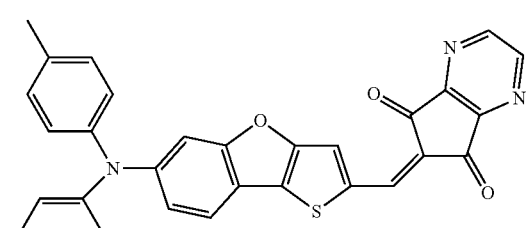
B-12
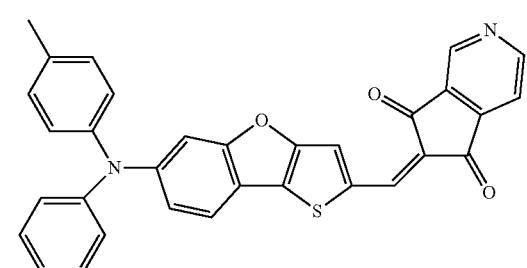
B-13
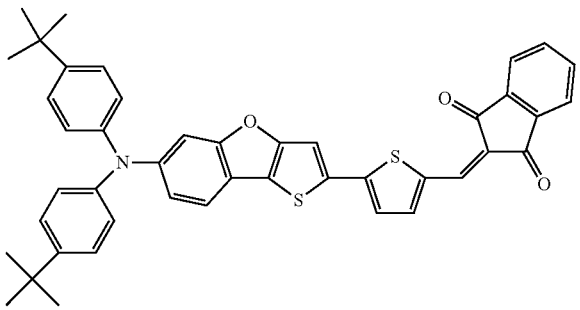
B-14
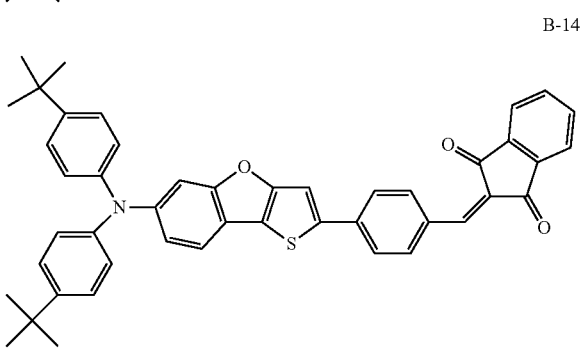

-continued
B-15
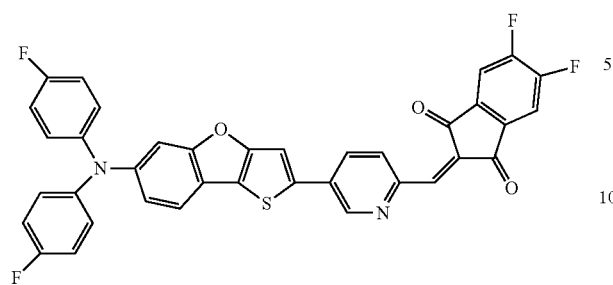
C-1
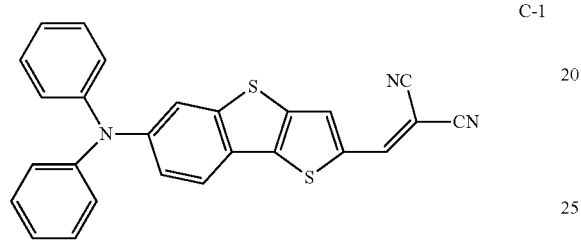
C-2
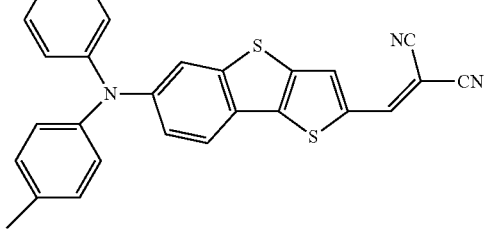
C-3
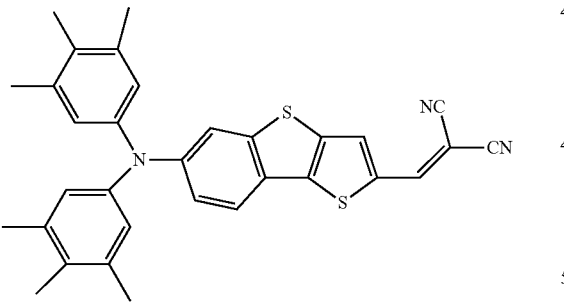
C-4
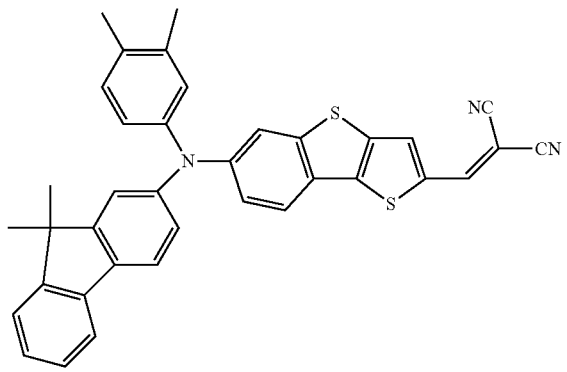
-continued
C-5
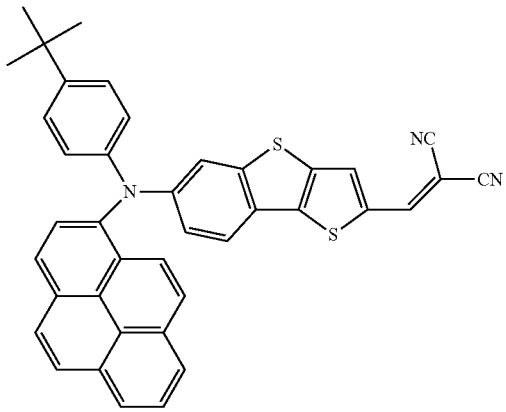
C-6
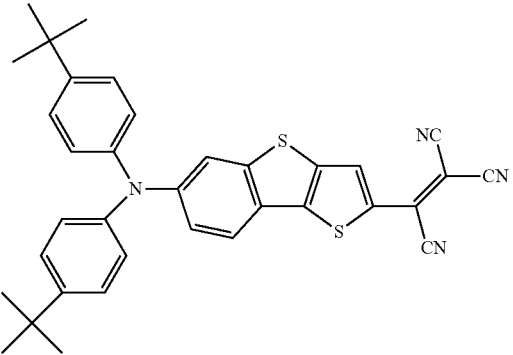
C-7
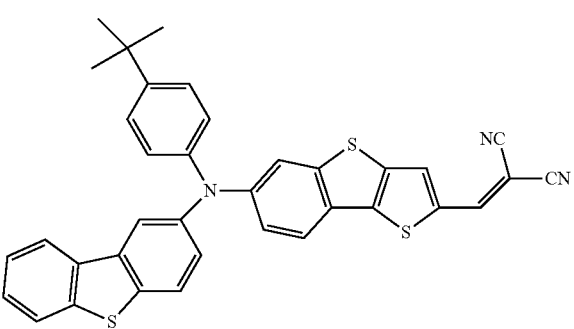
C-8
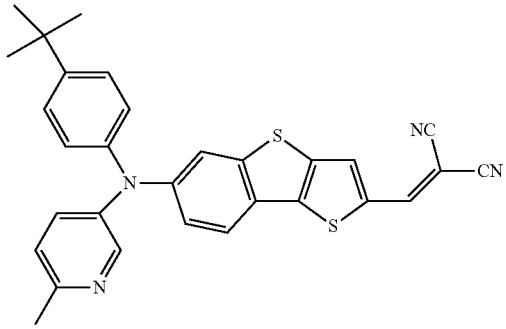

-continued
C-9
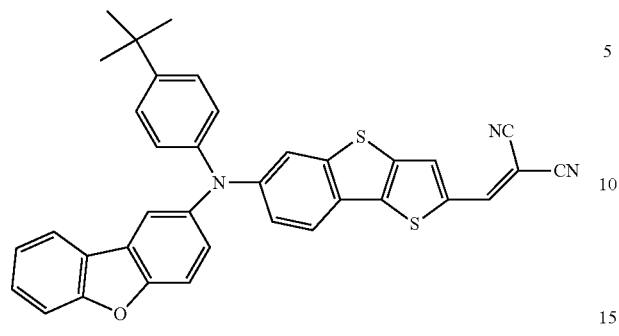
C-13
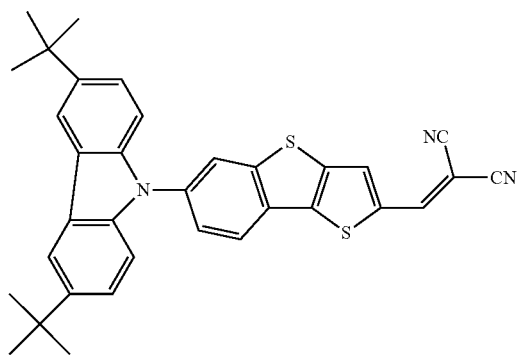
C-10
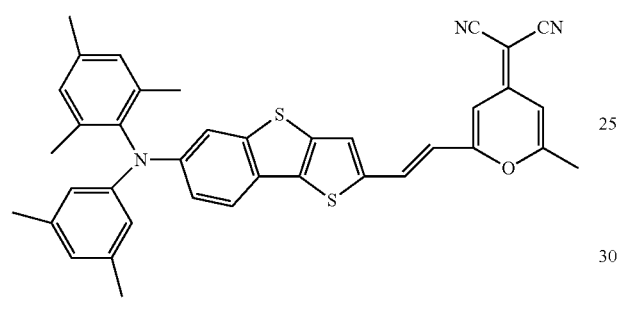
C-14
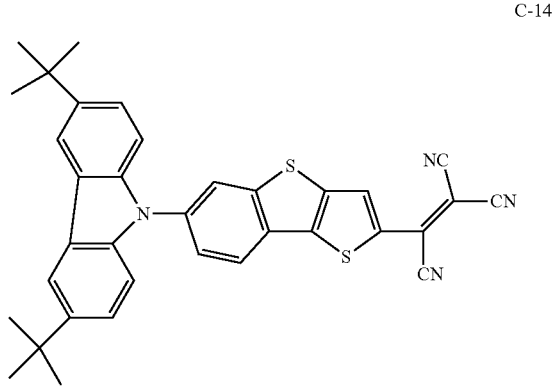
C-11
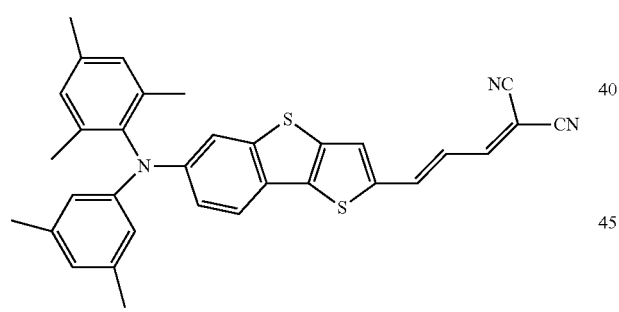
C-15
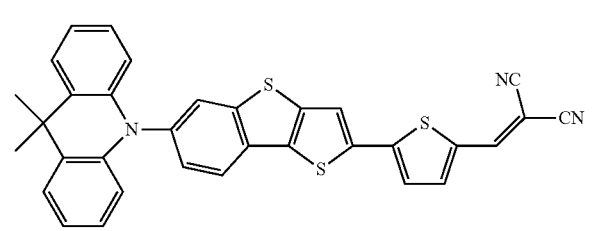
C-12
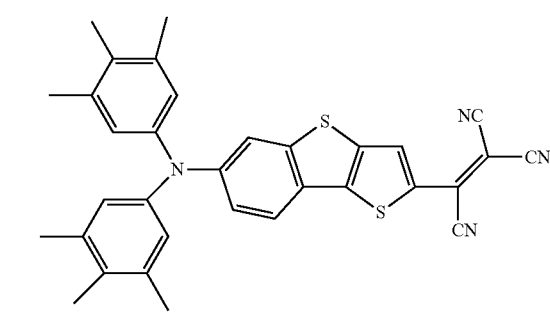
C-16
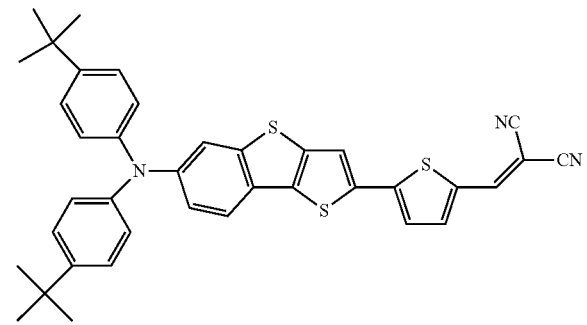

-continued
C-17
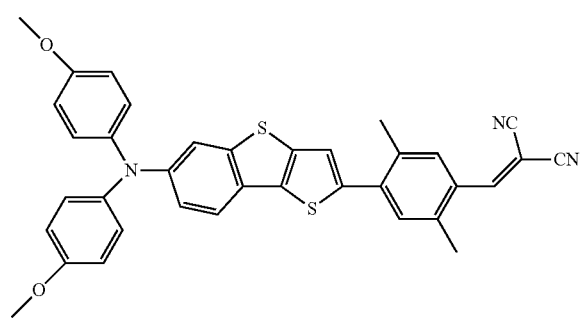
C-18
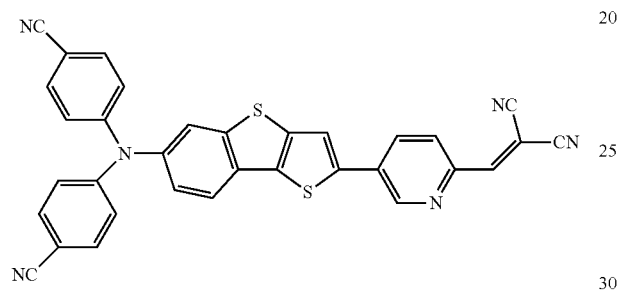
D-1
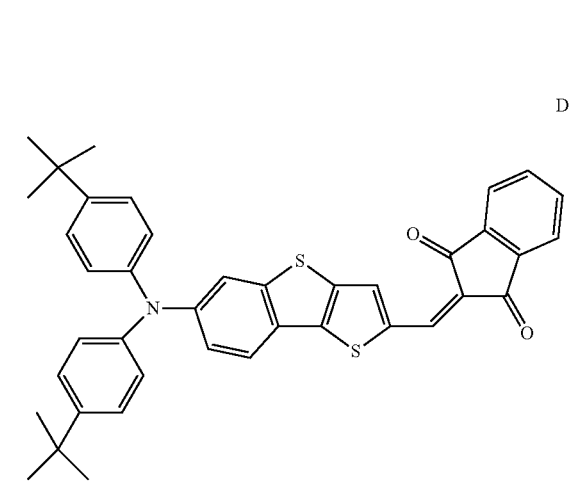
D-2
-continued
D-3
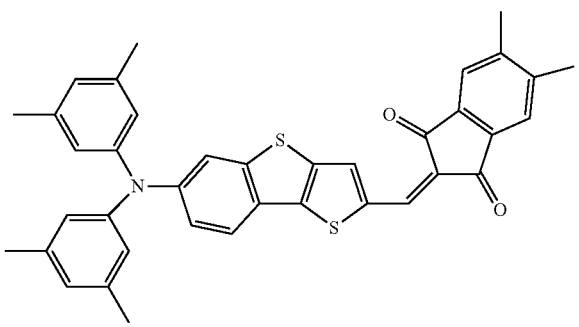
D-4
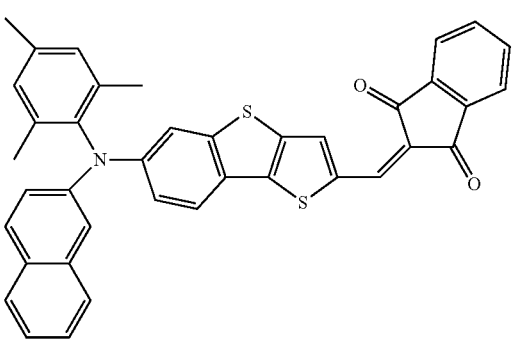
D-5
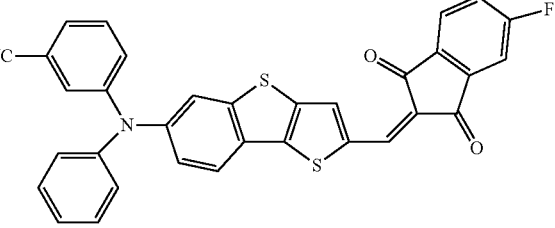
D-6
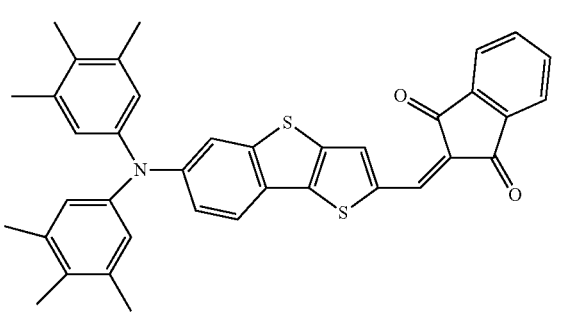
D-7
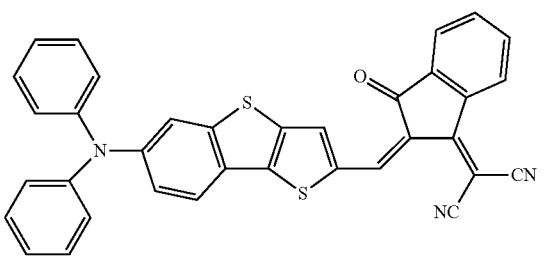

D-8
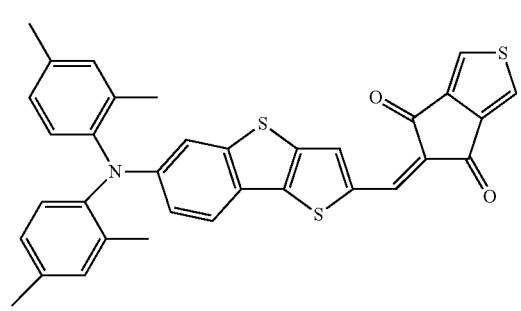
D-9
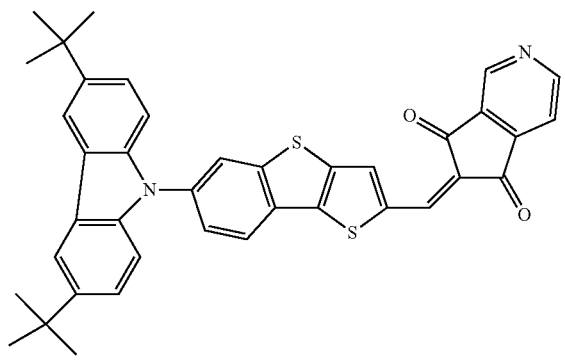
D-10
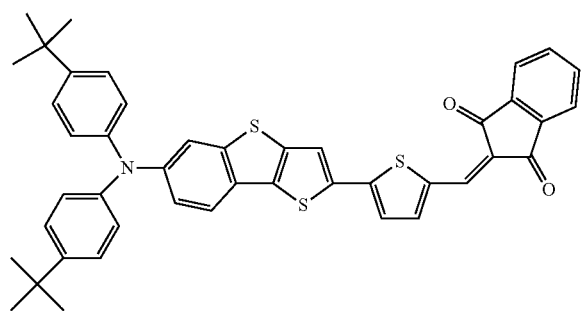
D-11
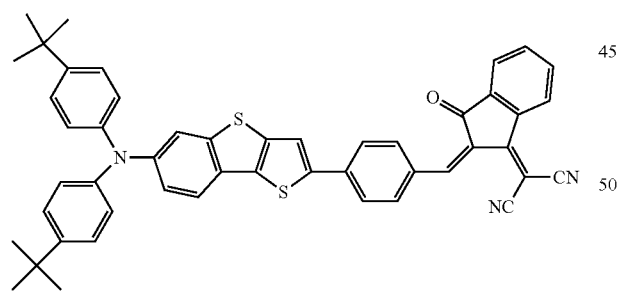
D-12
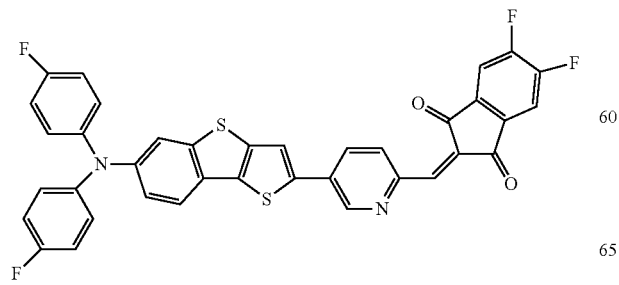
E-1
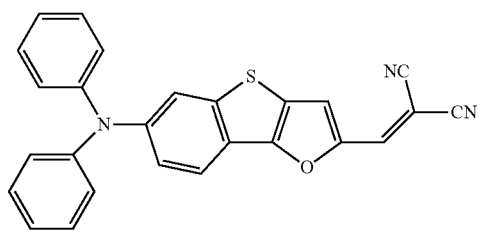
E-2
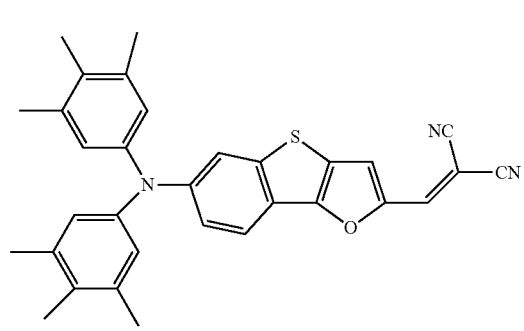
E-3
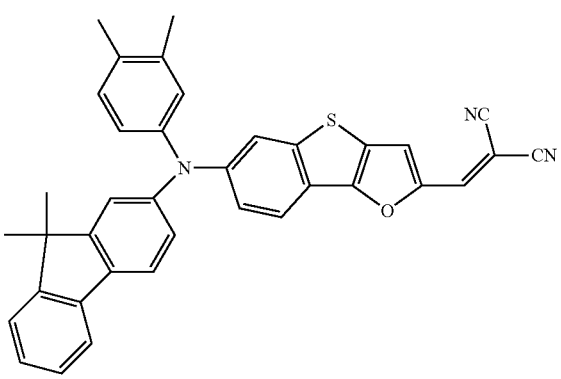
E-4
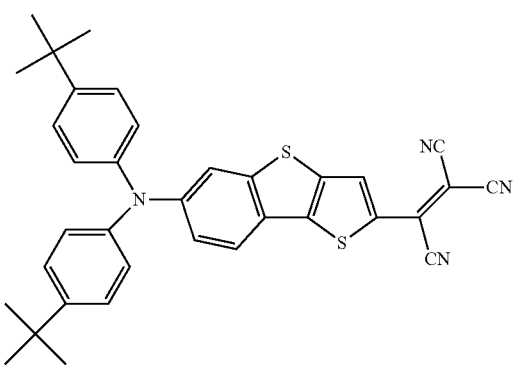

-continued
E-5
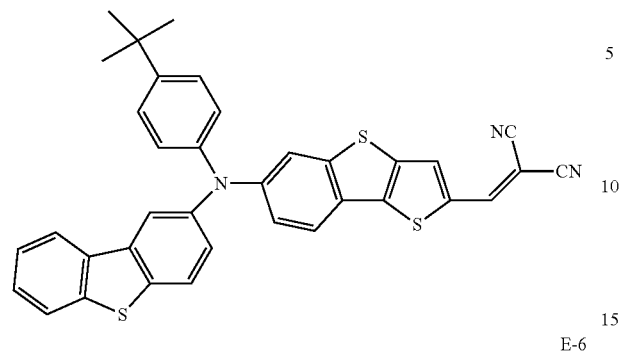
E-6
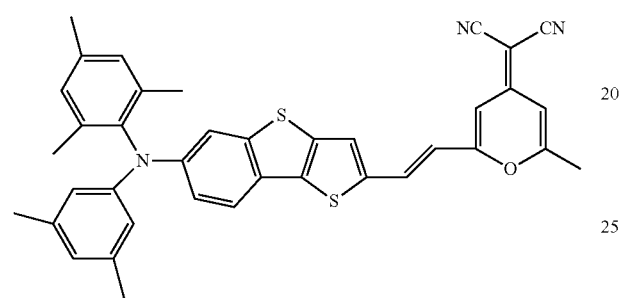
E-7
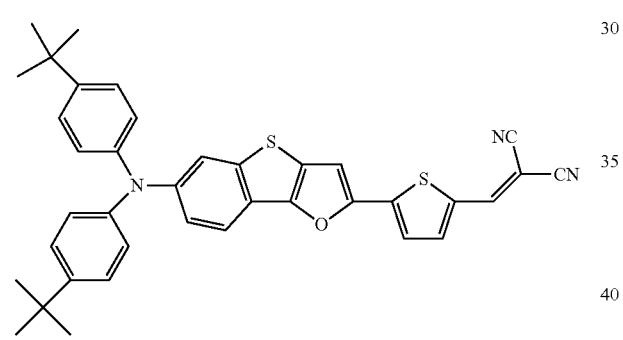
E-8
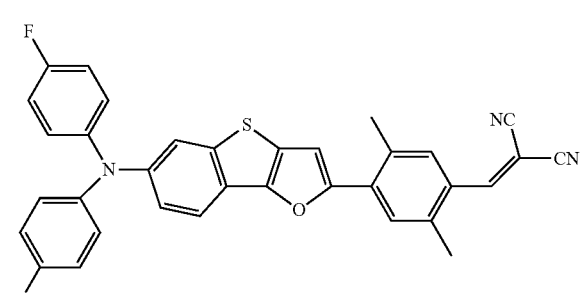
E-9
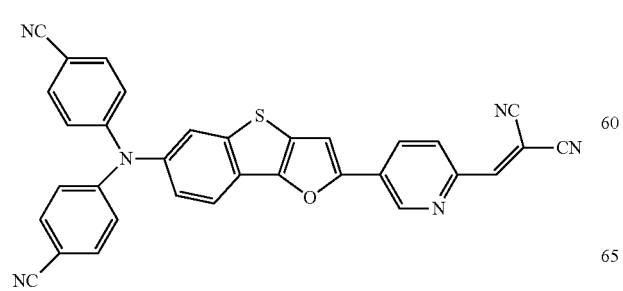
-continued
F-1
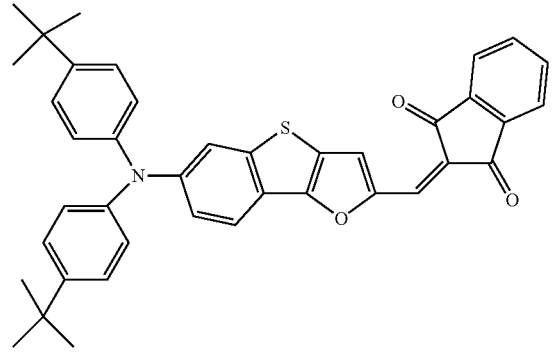
F-2
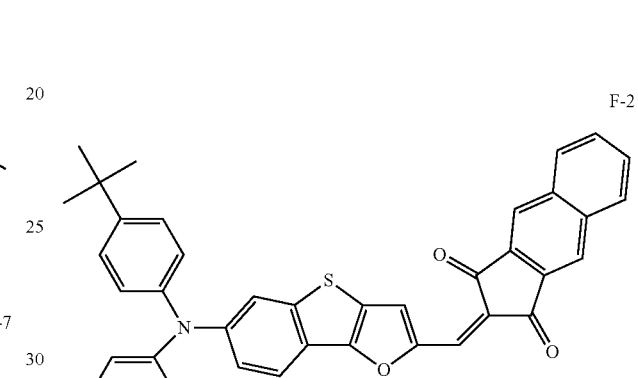
F-3
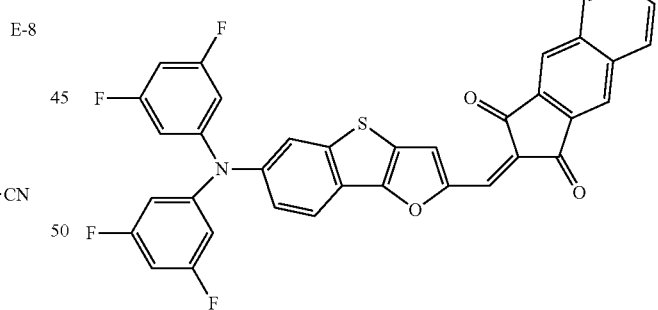
F-4
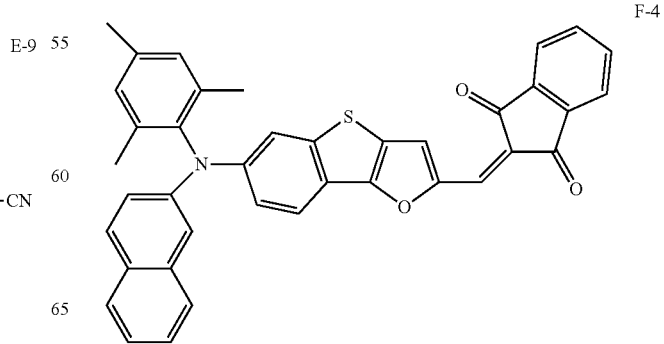

-continued
F-5
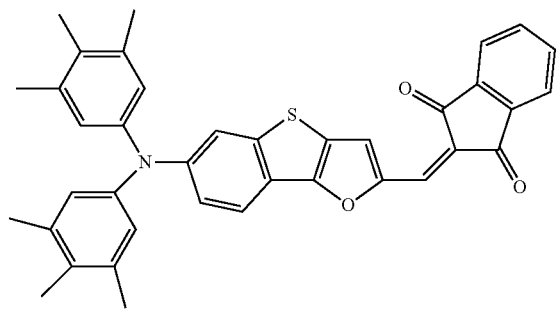
F-6
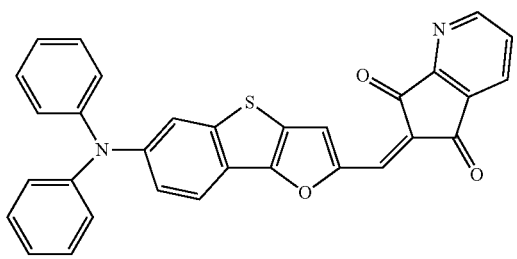
F-7
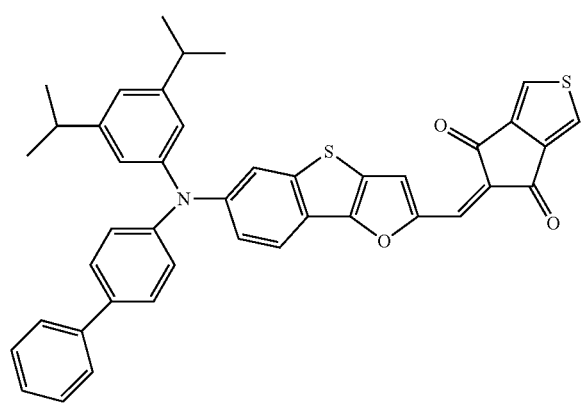
F-8
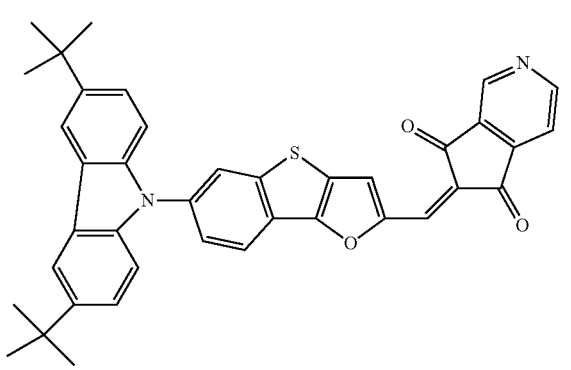
-continued
F-9
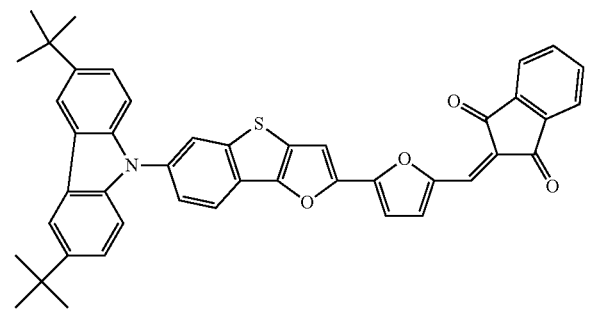
G-1
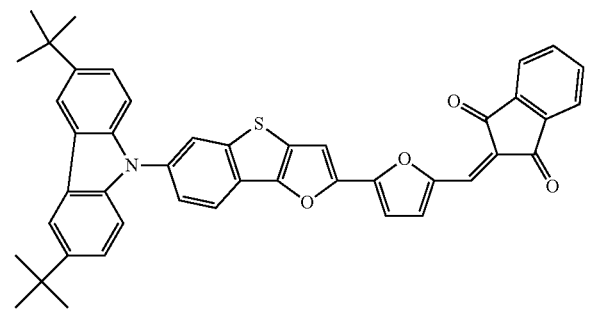
G-2
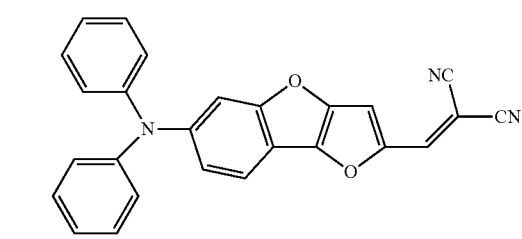
G-3
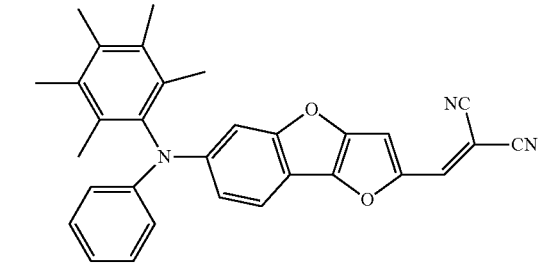
G-4
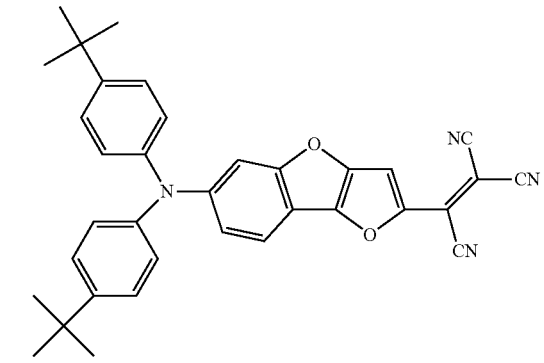

G-5
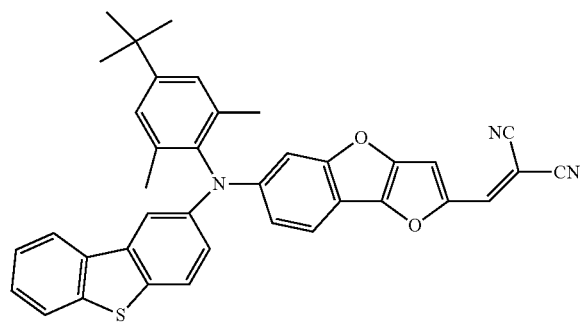

G-6
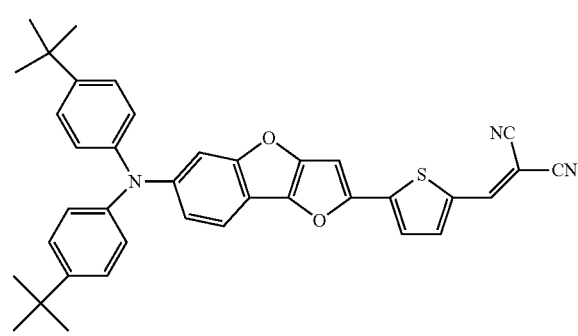

H-1
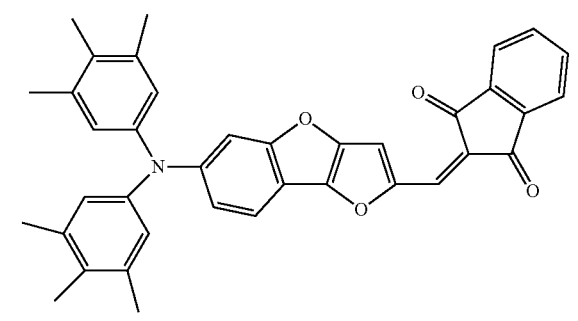

H-2
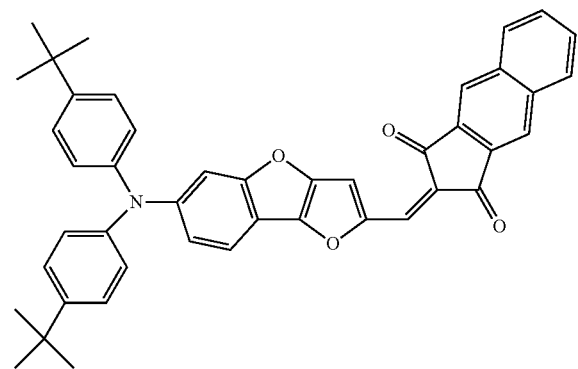

H-3
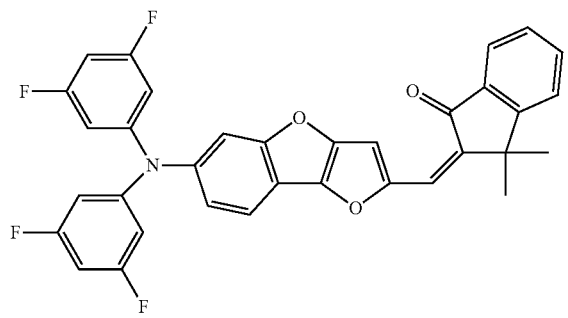
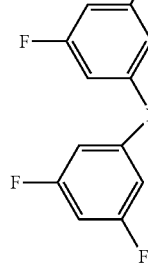

H-4
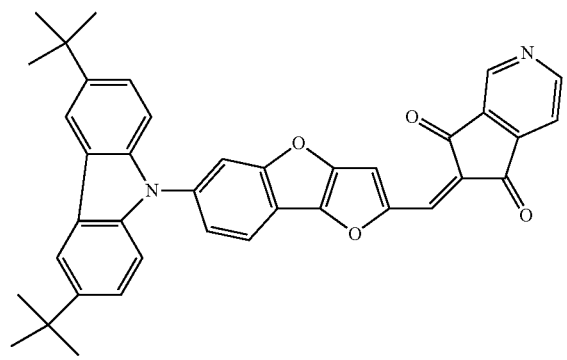

H-5
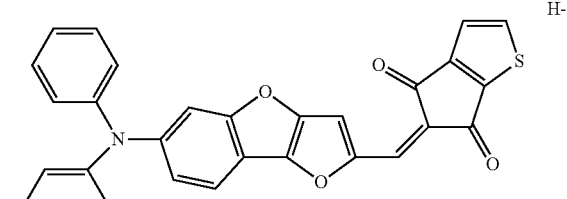

H-6
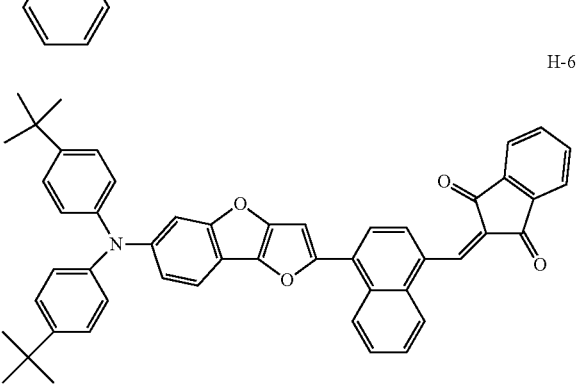

In each of the compounds shown in the groups A and B out of the exemplified compounds, the $X_1$ in the general formula [1] represents oxygen and the $X_2$ therein represents sulfur. A furan ring is a structure that narrows a five-membered ring and a thiophene ring is a structure that widens a five-membered ring. Accordingly, when the two rings are condensed with a benzene ring, a structure having small strain is formed, and hence the structural stability of any such compound is high.

In each of the compounds shown in the groups C and D, the $X_1$ in the general formula [1] represents sulfur and the $X_2$ therein represents sulfur. A thiophene ring oxidizes more hardly than a furan ring does.

In each of the compounds shown in the groups E and F, the $X_1$ in the general formula [1] represents sulfur and the $X_2$ therein represents oxygen. A furan ring is a structure that narrows a five-membered ring and a thiophene ring is a structure that widens a five-membered ring. Accordingly, when the two rings are condensed with a benzene ring, a structure having small strain is formed, and hence the structural stability of any such compound is high.

In each of the compounds shown in the groups G and H, the $X_1$ in the general formula [1] represents oxygen and the $X_2$ therein represents oxygen. The electronegativity of oxygen is higher than that of sulfur, and hence the dipole moments of the compounds are high.

In each of the compounds shown in the groups A, C, E, and G, the Q in the general formula [1] represents a group represented by the formula [1-1], and the group is a substituent having a small molecular weight. Accordingly, the compounds can be sublimated at low temperatures.

In each of the compounds shown in the groups B, D, F, and H, the Q in the general formula [1] represents a group represented by the formula [1-2]. In addition, particularly when the $R_8$ and the $R_9$ are bonded to each other to form a ring like the general formulae [2-1] to [2-9] and the general formula [2], the compounds are each increased in glass transition temperature to form a stable amorphous film.

[Method of Synthesizing Organic Compound According to Embodiment of the Present Disclosure]

Next, a method of synthesizing the organic compound according to the embodiment of the present disclosure is described, but the compound may be synthesized by utilizing any other synthesis method.

The thienobenzofuran skeleton serving as the basic skeleton of the organic compound according to the embodiment of the present disclosure can be synthesized in accordance with, for example, a synthesis scheme 1 shown below.

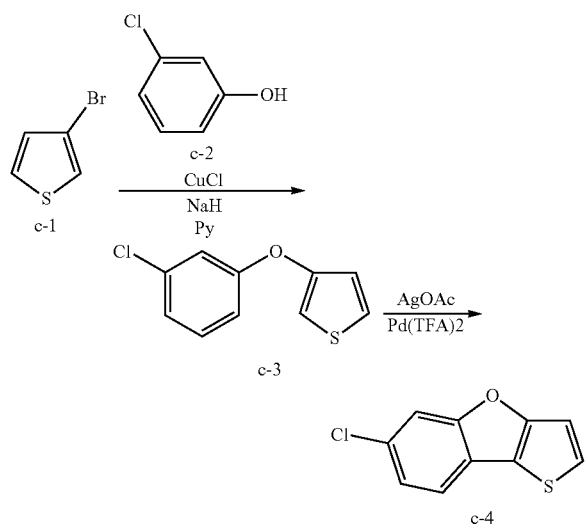

c-3 is derived by a coupling reaction using a CuCl catalyst. A thienobenzofuran skeleton c-4 is formed by a cyclization reaction using silver acetate and a palladium catalyst subsequent thereto.

The introduction of an amino group and an electron-withdrawing group into the thienobenzofuran skeleton can be performed by the following synthesis scheme 2.

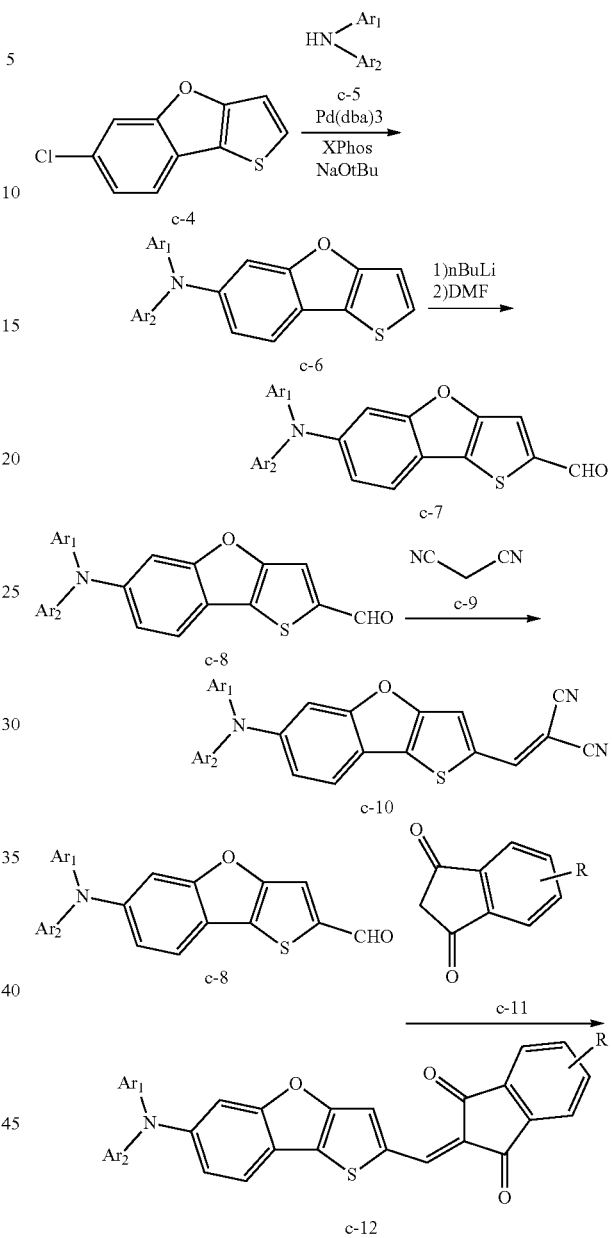

A diarylamino intermediate c-6 can be synthesized by an amination reaction between the basic skeleton (thienobenzofuran) intermediate c-4 and a diarylamino raw material c-5 using a palladium catalyst. For example, when a dicyano group is introduced as the electron-withdrawing group, a compound c-10 according to the embodiment of the present disclosure can be synthesized by causing an electron-withdrawing group raw material c-9 to react with a base, such as triethylamine or piperidine. In addition, for example, when a benzoindane group is introduced, a compound c-12 according to the embodiment of the present disclosure can be synthesized by causing an electron-withdrawing group raw material c-11 to react with a base, such as triethylamine or piperidine.

The thienobenzothiophene skeleton serving as the basic skeleton of the organic compound according to the embodiment of the present disclosure can be synthesized in accordance with, for example, a synthesis scheme 3 shown below.

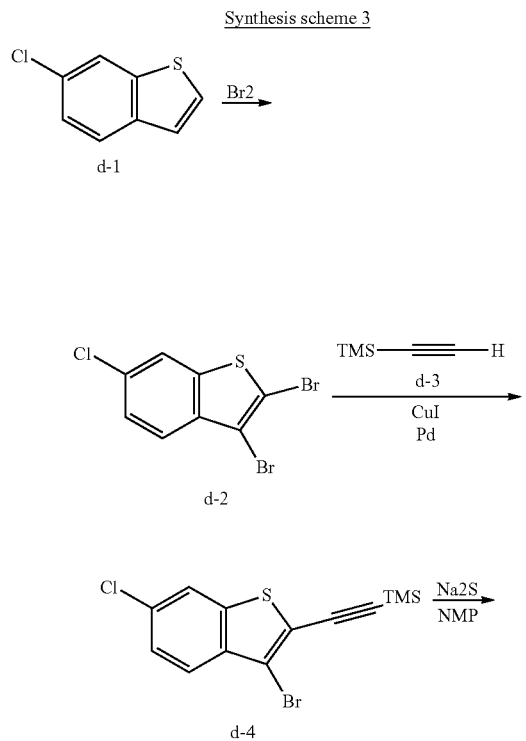

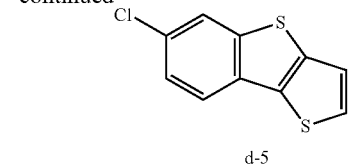

A benzothiophene intermediate d-4 is derived, and the thienobenzothiophene skeleton is formed by a reaction using $Na_2S$. An amino group and an electron-withdrawing group can be introduced in the same manner as in the synthesis scheme 2. Thus, the organic compound according to the embodiment of the present disclosure can be synthesized.

A furanobenzofuran skeleton serving as the basic skeleton of the organic compound according to the embodiment of the present disclosure can be synthesized by changing 2-bromothiophene serving as an intermediate c-1 to 2-bromofuran. In addition, an amino group and an electron-withdrawing group can be introduced in the same manner as in the synthesis scheme 2. Thus, the organic compound according to the embodiment of the present disclosure can be synthesized.

The organic compound according to the embodiment of the present disclosure can be synthesized by changing each of the basic skeleton intermediate, the diarylamino raw material, and the electron-withdrawing group raw material in accordance with the foregoing reaction scheme. Specific examples thereof are shown in Table 2 to Table 5.

TABLE 2

| | Basic skeleton intermediate | Diarylamino raw material | Electron-withdrawing group raw material | Exemplified Compound No. |
| --- | --- | --- | --- | --- |
| 1 | (Cl-benzofuranothiophene) | (diphenylamine) | NC–CN | A-1 |
| 2 | (Cl-benzofuranothiophene) | (trimethylphenyl-naphthylamine) | NC–CN | A-5 |

TABLE 2-continued
| | Basic skeleton intermediate | Diarylamino raw material | Electron-withdrawing group raw material | Exemplified Compound No. |
|---|---|---|---|---|
| 3 | 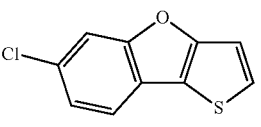 | 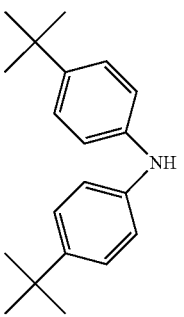 [SMILES: CC(C)(C)c1ccc(Nc2ccc(C(C)(C)C)cc2)cc1] | 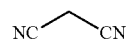 | A-6 |
| 4 | 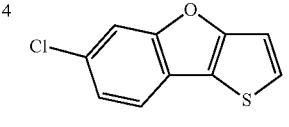 | 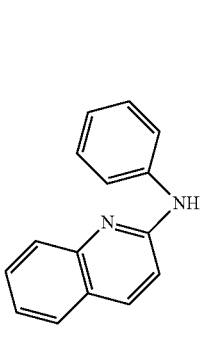 [SMILES: c1ccc(Nc2ccc3ccccc3n2)cc1] | 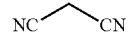 | A-7 |
| 5 | 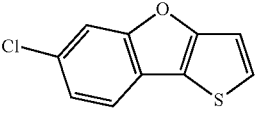 [SMILES: Clc1ccc2c(c1)oc1ccsc12] | 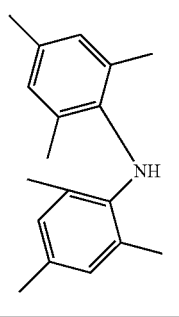 | 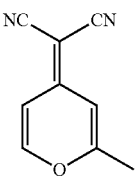 | A-10 |
TABLE 3
| | Basic skeleton intermediate | Diarylamino raw material | Electron-withdrawing group raw material | Exemplified Compound No. |
|---|---|---|---|---|
| 6 | 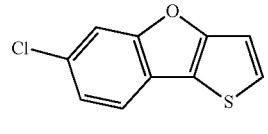 | 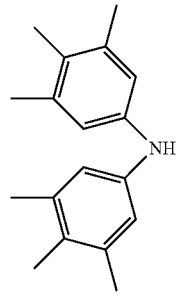 [SMILES: Cc1cc(Nc2cc(C)c(C)c(C)c2)cc(C)c1C] | 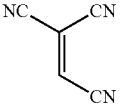 | A-12 |

TABLE 3-continued
| | Basic skeleton intermediate | Diarylamino raw material | Electron-withdrawing group raw material | Exemplified Compound No. |
|---|---|---|---|---|
| 7 | 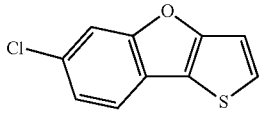 [SMILES: Clc1ccc2c(c1)oc1ccsc12] | 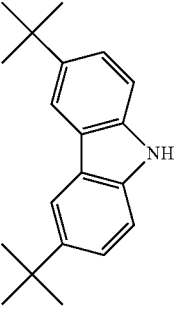 [SMILES: CC(C)(C)c1ccc2[nH]c3ccc(C(C)(C)C)cc3c2c1] | 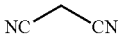 | A-13 |
| 8 | 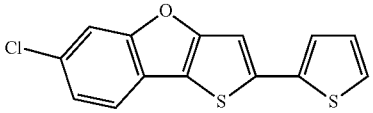 [SMILES: Clc1ccc2c(c1)oc1cc(-c3cccs3)sc12] | 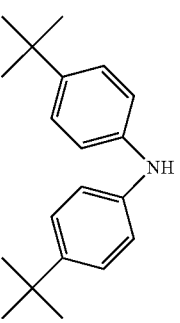 [SMILES: CC(C)(C)c1ccc(Nc2ccc(C(C)(C)C)cc2)cc1] | 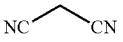 | A-16 |
| 9 | 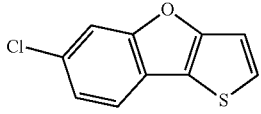 | 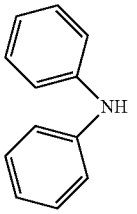 [SMILES: c1ccc(Nc2ccccc2)cc1] | 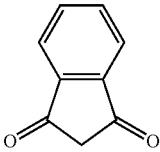 [SMILES: O=C1CC(=O)c2ccccc21] | B-1 |
| 10 | 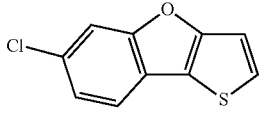 [SMILES: Clc1ccc2c(c1)oc1ccsc12] | 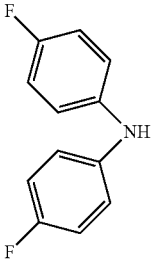 | 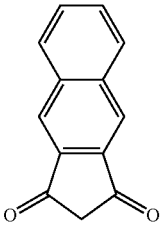 [SMILES: O=C1CC(=O)c2cc3ccccc3cc21] | B-9 |
| 11 | 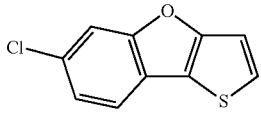 | 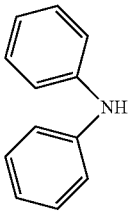 | 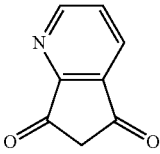 [SMILES: O=C1CC(=O)c2ncccc21] | B-10 |

TABLE 4
| | Basic skeleton intermediate | Diarylamino raw material | Electron-withdrawing group raw material | Exemplified Compound No. |
|---|---|---|---|---|
| 12 | 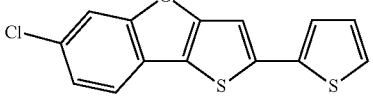 | 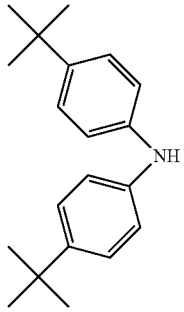 [SMILES: CC(C)(C)c1ccc(Nc2ccc(C(C)(C)C)cc2)cc1] | 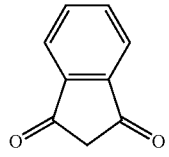 | B-13 |
| 13 | 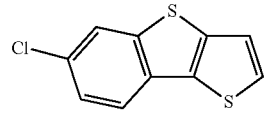 | 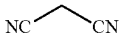 | 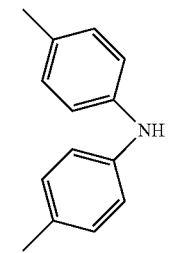 | C-2 |
| 14 | 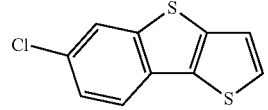 [SMILES: Clc1ccc2c(c1)sc1ccsc12] | 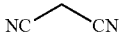 | 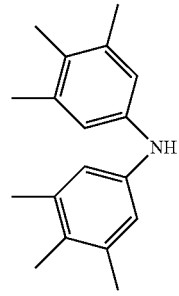 [SMILES: Cc1cc(Nc2cc(C)c(C)c(C)c2)cc(C)c1C] | C-3 |
| 15 | 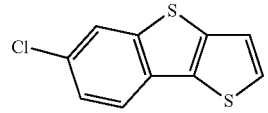 [SMILES: Clc1ccc2c(c1)sc1ccsc12] |  | 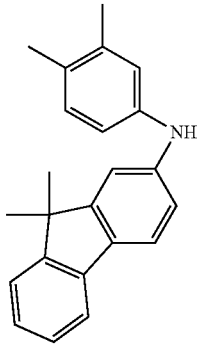 [SMILES: Cc1ccc(Nc2ccc3c(c2)C(C)(C)c2ccccc2-3)cc1C] | C-4 |

TABLE 4-continued
| | Basic skeleton intermediate | Diarylamino raw material | Electron-withdrawing group raw material | Exemplified Compound No. |
|---|---|---|---|---|
| 16 | 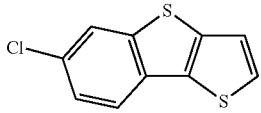 [SMILES: Clc1ccc2c(c1)sc1ccsc12] | 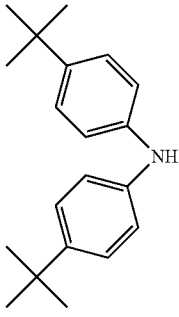 | 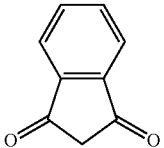 | D-1 |
| 17 | 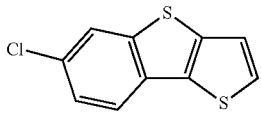 [SMILES: Clc1ccc2c(c1)sc1ccsc12] | 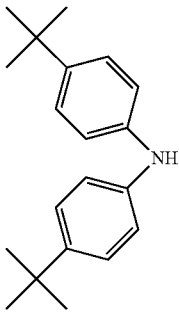 [SMILES: CC(C)(C)c1ccc(Nc2ccc(C(C)(C)C)cc2)cc1] | 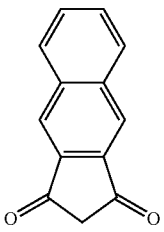 | D-2 |
TABLE 5
| | Basic skeleton intermediate | Diarylamino raw material | Electron-withdrawing group raw material | Exemplified Compound No. |
|---|---|---|---|---|
| 18 | 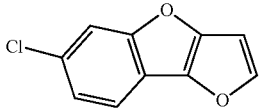 [SMILES: Clc1ccc2c(c1)oc1ccoc12] | 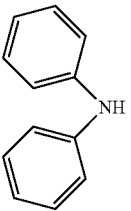 [SMILES: c1ccc(Nc2ccccc2)cc1] |  | G-1 |
| 19 | 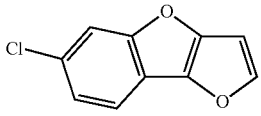 | 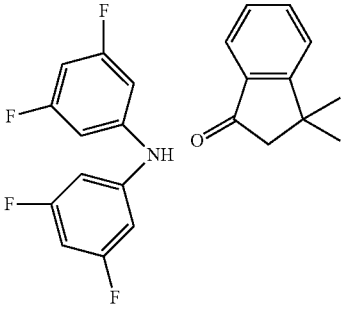 | 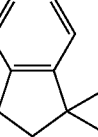 | H-3 |

[Photoelectric Conversion Element According to Embodiment of the Present Disclosure]

(1) Photoelectric Conversion Element

Figure 2:
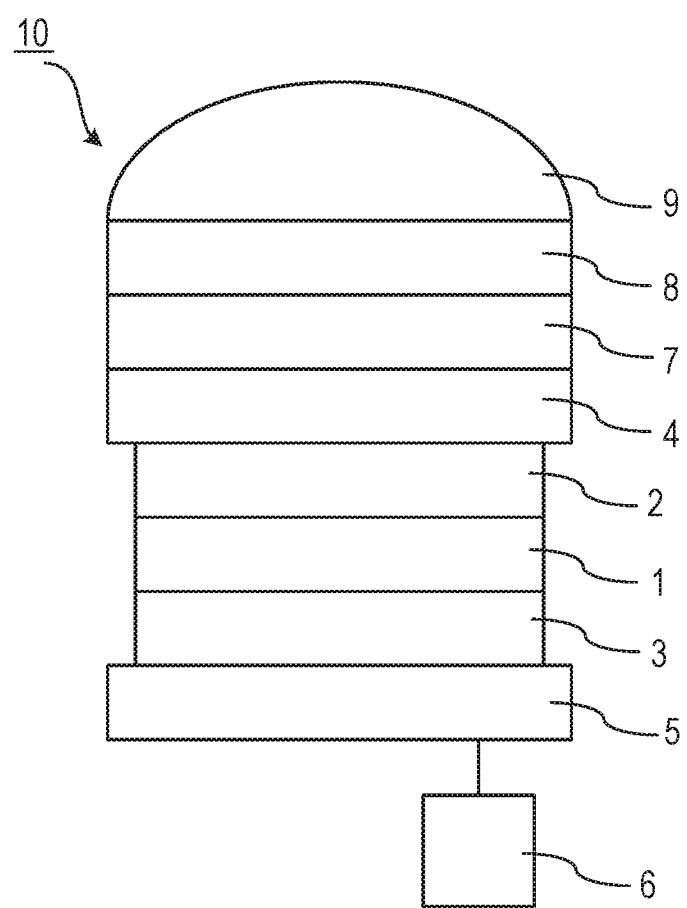
FIG. 2 is a schematic sectional view for illustrating an example of a photoelectric conversion element according to an embodiment of the present disclosure.

A photoelectric conversion element according to an embodiment of the present disclosure includes an anode, a cathode, and an organic compound layer arranged between the anode and the cathode, and the organic compound layer has a first organic layer containing the organic compound according to the embodiment of the present disclosure. FIG. 2 is a schematic sectional view for illustrating an example of the photoelectric conversion element according to the embodiment of the present disclosure. In a photoelectric conversion element 10, an organic compound layer is arranged between an anode 5 and a cathode 4, and the organic compound layer has a first organic layer 1 containing the organic compound according to the embodiment of the present disclosure. The first organic layer 1 is a layer configured to form a photoelectric conversion portion configured to convert light into charge. In view of the foregoing, the first organic layer 1 can also be referred to as "photoelectric conversion layer." When the photoelectric conversion element 10 has a plurality of layers, the plurality of layers are preferably laminated in a direction from the anode 5 to the cathode 4. The organic compound layer may have: a second organic layer 2 arranged between the first organic layer 1 and the cathode 4; and a third organic layer 3 arranged between the first organic layer 1 and the anode 5. A protective layer 7, a wavelength-selecting portion 8, and a microlens 9 are arranged on the cathode 4. A readout circuit 6 is connected to the anode 5. The photoelectric conversion element 10 may be formed on a substrate (not shown). When the photoelectric conversion element 10 performs photoelectric conversion, a voltage may be applied between the anode 5 and the cathode 4. The voltage is preferably about 1 V or more and about 15 V or less, though the preferred voltage varies depending on the total thickness of the organic compound layer. The voltage is more preferably about 2 V or more and about 10 V or less.

(2) Substrate

The photoelectric conversion element according to the embodiment of the present disclosure may include a substrate. Examples of the substrate include a glass substrate, a flexible substrate, and a semiconductor substrate.

In addition, the photoelectric conversion element according to the embodiment of the present disclosure may include a semiconductor substrate. A constituent element for the semiconductor substrate is not limited as long as a charge-storing portion and a floating diffusion (FD) can be formed by the injection of impurities. Examples thereof include Si, GaAs, and GaP. Of those, Si is particularly preferred. The semiconductor substrate may be an N-type epitaxial layer. In that case, a P-type well, an N-type well, a P-type semiconductor region, and an N-type semiconductor region are arranged on the semiconductor substrate.

The charge-storing portion is an N-type semiconductor region or P-type semiconductor region formed on the semiconductor substrate by ion implantation, and is a region configured to store charge generated in the photoelectric conversion portion. When an electron is stored, the N-type semiconductor region may be formed on the surface of the semiconductor substrate, or a storage diode of a PN structure may be formed from the surface of the substrate. In each case, an electron can be stored in the N-type semiconductor region. Meanwhile, when a hole is stored, the P-type semiconductor region may be formed on the surface of the semiconductor substrate, or a storage diode of an NP structure may be formed from the surface of the substrate. In each case, an electron can be stored in the P-type semiconductor region.

The stored charge is transferred from the charge-storing portion to the FD. The charge transfer may be controlled by a gate electrode. The charge generated in the first organic layer 1 is stored in the charge-storing portion, and the charge stored in the charge-storing portion is transferred to the FD. After that, the charge is converted into a current by an amplification transistor (FIG. 3) to be described later. In addition, when the charge-storing portion forms a PN junction, the photoelectric conversion may be performed by light leaking from the photoelectric conversion portion. The photoelectric conversion element may include a charge-outputting portion without including the charge-storing portion. When the element includes the outputting portion, the charge generated in the first organic layer 1 is transferred from an electrode to the amplification transistor or the like without through the FD.

(3) Anode (Electron-Collecting Electrode) 5 and Cathode (Hole-Collecting Electrode) 4

The anode 5 is an electrode configured to collect an electron out of the charge generated in the first organic layer 1. The anode may be a pixel electrode in the construction of an imaging device. The anode 5 may be arranged on a side closer to a pixel circuit with respect to the cathode 4. The anode 5 can be called an electron-collecting electrode because of its function. A constituent material for the anode 5 is, for example, indium tin oxide (ITO), indium zinc oxide, $SnO_2$, antimony-doped tin oxide (ATO), ZnO, Al-doped zinc oxide (AZO), gallium-doped zinc oxide (GZO), $TiO_2$, or fluorine-doped tin oxide (FTO).

The cathode 4 is an electrode configured to collect a hole out of the charge generated in the first organic layer 1. The cathode may be a pixel electrode in the construction of the imaging device. A constituent material for the cathode 4 is, for example, a metal, a metal oxide, a metal nitride, a metal boride, an organic conductive compound, or a mixture obtained by combining two or more kinds thereof. Specific examples thereof include: conductive metal oxides, such as antimony-doped or fluorine-doped tin oxide (ATO or FTO), tin oxide, zinc oxide, indium oxide, indium tin oxide (ITO), and indium zinc oxide; metal materials, such as gold, silver, magnesium, chromium, nickel, titanium, tungsten, and aluminum; conductive compounds, such as oxides or nitrides of these metal materials (e.g., titanium nitride (TiN)); mixtures or laminates of these metals and the conductive metal oxides; inorganic conductive substances, such as copper iodide and copper sulfide; organic conductive materials, such as polyaniline, polythiophene, and polypyrrole; and laminates of these substances or materials and ITO or titanium nitride. The constituent material for the cathode 4 is particularly preferably a material selected from the group consisting of an alloy of magnesium and silver, titanium nitride, molybdenum nitride, tantalum nitride, and tungsten nitride.

The pixel electrode may be any one of the anode 5 and the cathode 4. The transparency of an electrode on a light extraction side is preferably high. The transparency is specifically 80% or more. In addition, an electrode on a light incident side can also be referred to as "upper electrode." In that case, the other electrode is referred to as "lower electrode."

A method of forming each of the above-mentioned two kinds of electrodes (the anode and the cathode) can be appropriately selected in consideration of its suitability with an electrode material to be used. Specifically, the electrodes can be formed by, for example, a printing system, a wet system, such as a coating system, a physical system, such as a vacuum deposition method, a sputtering method, or an ion plating method, or a chemical system, such as CVD or a plasma CVD method. In the case where the electrodes are formed by using ITO, the electrodes can be formed by a method such as an electron beam method, the sputtering method, a resistance heating deposition method, a chemical reaction method (e.g., a sol-gel method), or the application of a dispersed product of indium tin oxide. In addition, in such case, the surfaces of the formed electrodes (ITO electrodes) may be subjected to, for example, a UV-ozone treatment or a plasma treatment. In the case where the electrodes are formed by using TiN, various film-forming methods typified by a reactive sputtering method can be used. In addition, in such case, the formed electrodes (TiN electrodes) may be subjected to, for example, an annealing treatment, the UV-ozone treatment, or the plasma treatment.

(4) First Organic Layer (Photoelectric Conversion Layer) 1

As described above, the first organic layer 1 can also be referred to as "photoelectric conversion layer." A constituent material for the first organic layer 1 of the photoelectric conversion element according to the embodiment of the present disclosure is described. The first organic layer 1 contains the organic compound according to the embodiment of the present disclosure. It is preferred that the first organic layer 1 have a high light absorptivity and perform the charge separation of received light efficiently, that is, have high photoelectric conversion efficiency. In addition, the layer is preferably capable of immediately transporting generated charge, that is, an electron and a hole to the electrodes. In addition, in order that a reduction in quality of the layer, such as crystallization, may be suppressed, a material having a high glass transition temperature is preferred. The layer may be a mixed layer of the organic compound and the material having a high glass transition temperature from the viewpoint of an improvement in quality thereof. The first organic layer 1 may contain a plurality of kinds of organic compounds. When the first organic layer 1 has a plurality of kinds of organic compounds, the plurality of kinds of organic compounds may be mixed in one layer, or the plurality of kinds of organic compounds may be incorporated into a plurality of layers.

The first organic layer 1 is preferably a layer containing an organic p-type compound, such as a p-type organic semiconductor, or an organic n-type compound, such as an n-type organic semiconductor, and more preferably includes a bulk hetero layer (mixed layer), which is obtained by mixing the organic p-type compound and the organic n-type compound, in at least part thereof. When the first organic layer 1 has the bulk hetero layer, its photoelectric conversion efficiency (sensitivity) can be improved. When the layer has the bulk hetero layer at an optimum mixing ratio, the electron mobility and hole mobility of the first organic layer 1 can be increased, and hence the optical response speed of the photoelectric conversion element can be increased.

The first organic layer 1 preferably contains a fullerene, a fullerene analog, or a fullerene derivative as an n-type organic semiconductor. A plurality of fullerene molecules, fullerene analog molecules, or fullerene derivative molecules form an electron path. Accordingly, the electron transportability of the layer is improved, and responsiveness of the photoelectric conversion element is improved. When the total amount of the photoelectric conversion layer is defined as 100%, the content of the fullerene, the fullerene analog, or the fullerene derivative is preferably 20 mass % or more and 80 mass % or less. The fullerene analog is a generic term for closed-shell cavity-shaped clusters each including only many carbon atoms, and examples thereof include fullerene C60, and fullerenes C70, C74, C76, and C78 serving as higher order fullerenes. Those materials may be used alone or in combination thereof. A material to be used as a material responsible for charge separation and electron carriage is not limited to the fullerene analog, and a plurality of other materials may be simultaneously used. A material except the fullerene is, for example, a naphthalene compound, such as NTCDI, a perylene compound, such as PTCDI, a phthalocyanine compound, such as SubPc, or a thiophene compound, such as DCV3T, the compounds being known as n-type organic semiconductors.

Examples of the fullerene analog include fullerene C60, fullerene C70, fullerene C76, fullerene C78, fullerene C80, fullerene C82, fullerene C84, fullerene C90, fullerene C96, fullerene C240, fullerene C540, mixed fullerene, and fullerene nanotubes. In addition, examples of the fullerene derivative include the following compounds.

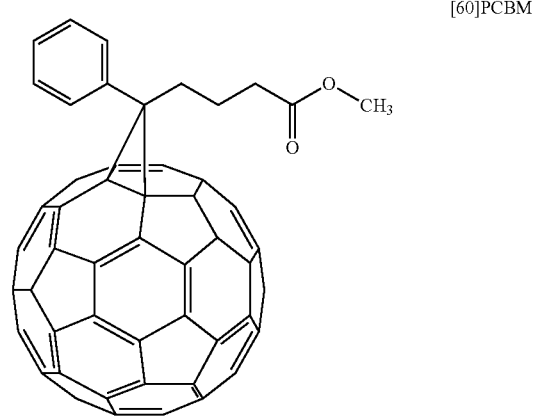

[60]PCBM

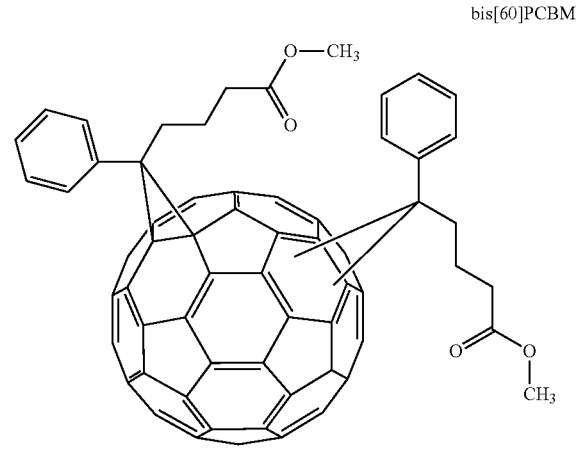

bis[60]PCBM

[70]PCBM

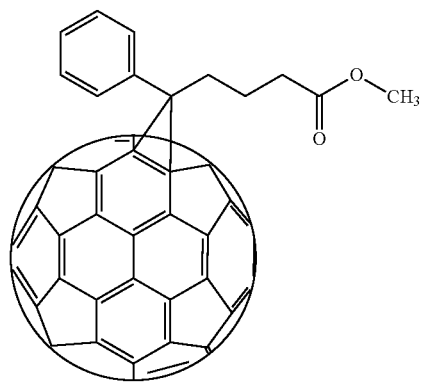

[60]ThCBM

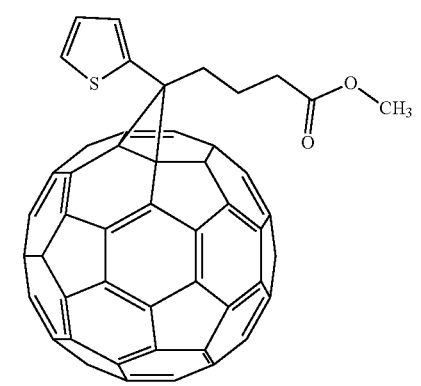

The first organic layer 1 may contain, for example, a p-type organic semiconductor in addition to the organic compound according to the embodiment of the present disclosure. Examples of such p-type organic semiconductor may include the following organic compounds. The compounds shown below may have substituents, such as an alkyl group, to the extent that their functions are not impaired.

CG1

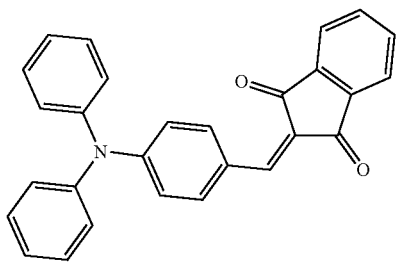

CG2

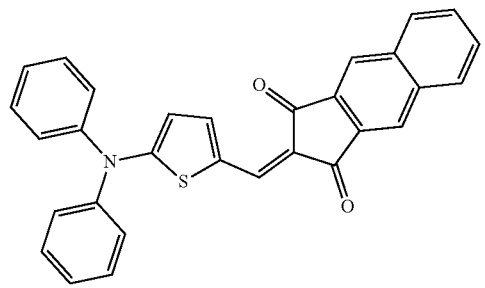

CG3

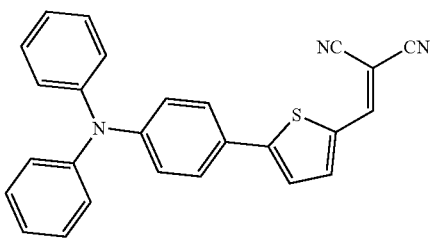

CG4

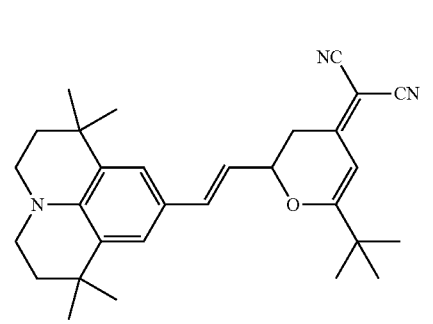

CG5

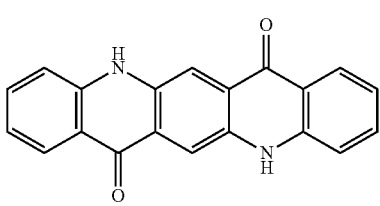

CG6

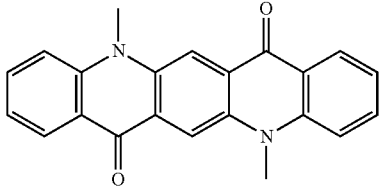

CG7

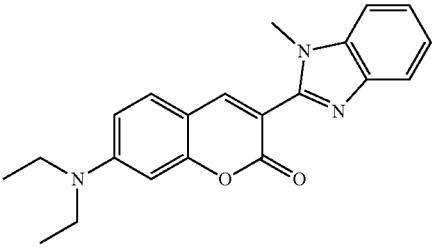

CG8

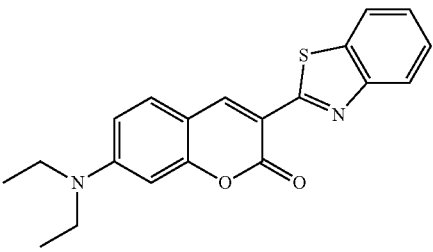

CG9
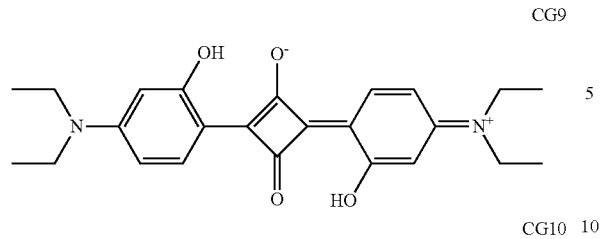
CG10
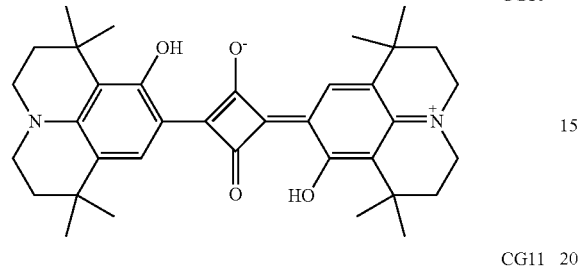
CG11
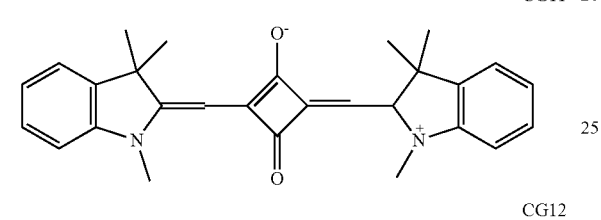
CG12
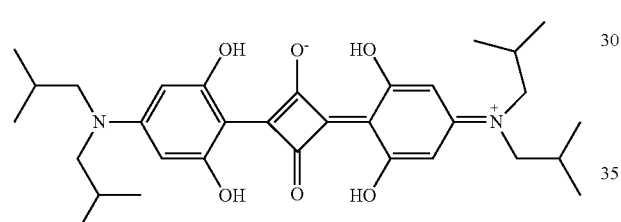
CG13
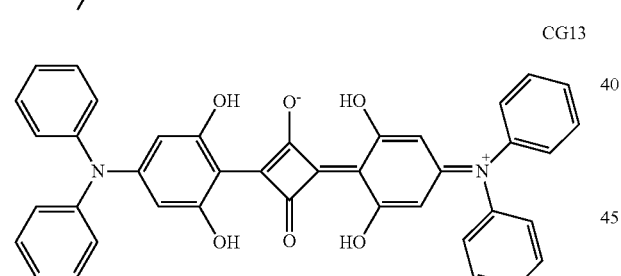
CG14
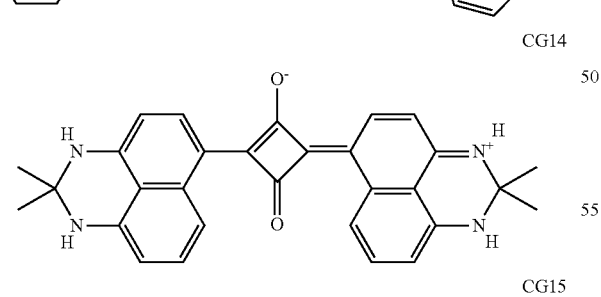
CG15
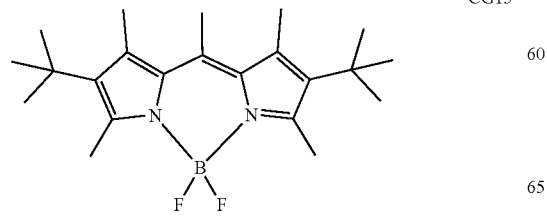
CG16
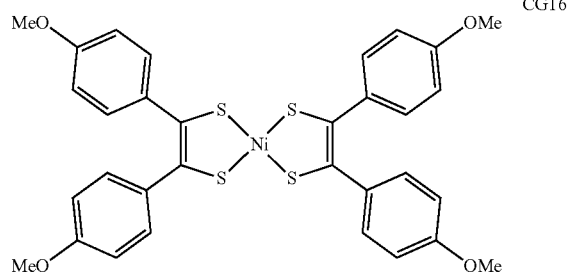
CG17
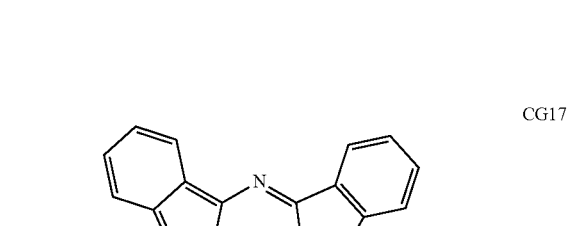
CG18
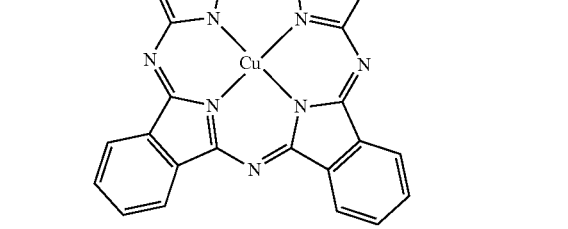
CG19
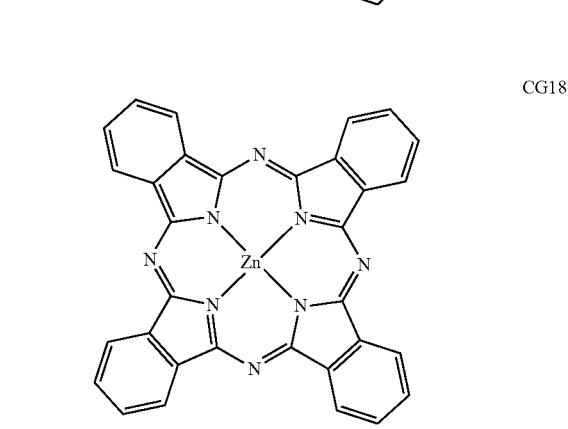
CG20
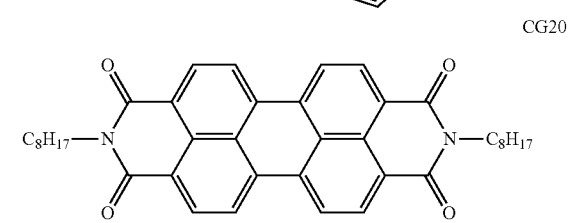

-continued
CG21
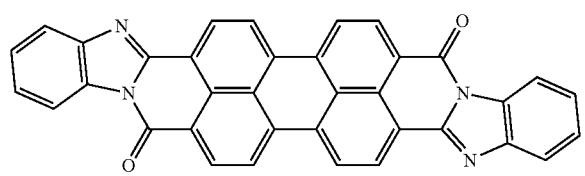
CG22
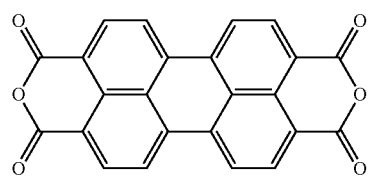
CG23
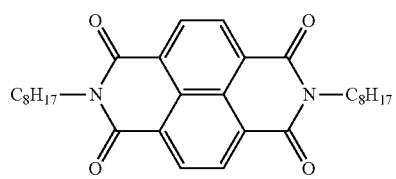
CG24
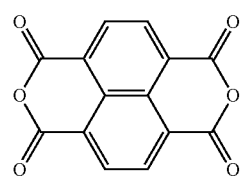
CG25
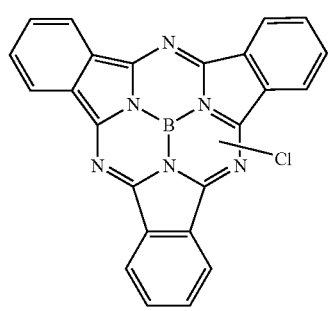
CG26
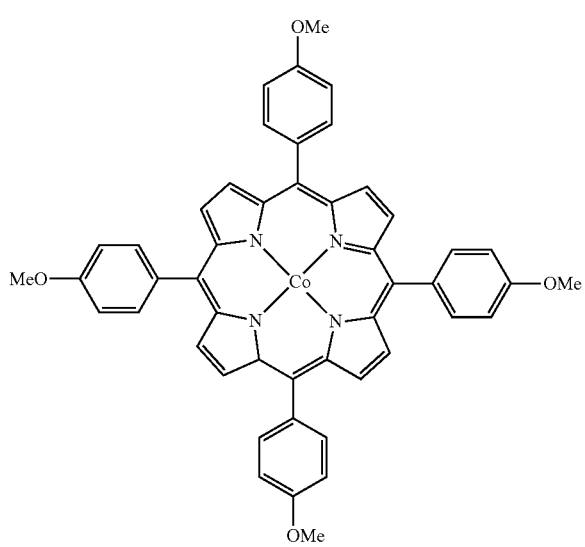
-continued
CG27
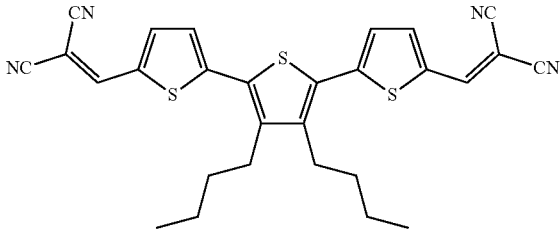
CG28
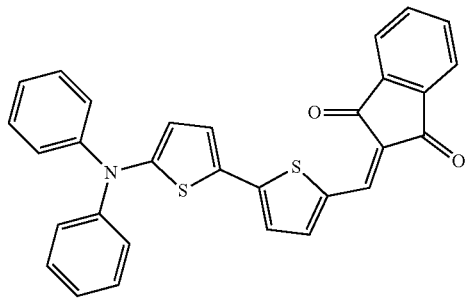
CG29
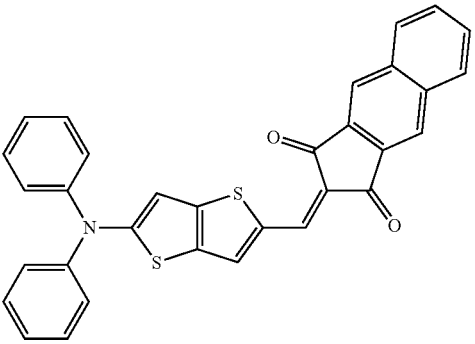
CG30
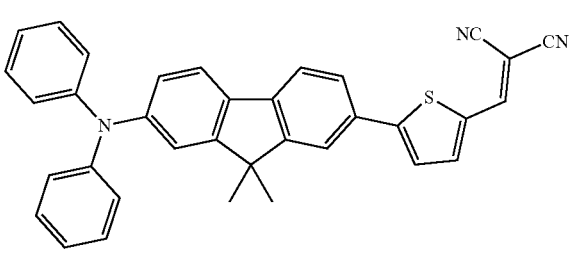
CG31

(5) Second Organic Layer (Electron-Blocking Layer) 2

The second organic layer 2 is a layer configured to suppress the flow of an electron from the cathode 4 into the first organic layer 1, and preferably has a small electron affinity (LUMO close to a vacuum level). A small electron affinity can be rephrased as a low LUMO. The second organic layer 2 can be called an electron-blocking layer because of its function. The second organic layer 2 may be a plurality of layers, or a bulk hetero layer (mixed layer) may be used as the layer. The photoelectric conversion element may include any other functional layer between the cathode 4 and the second organic layer 2.

(6) Third Organic Layer (Hole-Blocking Layer) 3

The third organic layer 3 is a layer configured to suppress the flow of a hole from the anode 5 into the first organic layer 1, and preferably has a large ionization potential (HOMO distant from the vacuum level). A large ionization potential can be rephrased as a high HOMO. The third organic layer 3 can be called a hole-blocking layer because of its function. The third organic layer 3 may be a plurality of layers, or a bulk hetero layer (mixed layer) may be used as the layer. The photoelectric conversion element may include any other functional layer between the anode 5 and the third organic layer 3.

(7) Protective Layer 7

The protective layer 7 is a layer to be formed above the electrodes, and is preferably an insulating layer. The protective layer 7 may be formed of a single material, or may include a plurality of materials. When the layer includes a plurality of materials, the layer may be obtained by laminating a plurality of layers, or may be a layer obtained by mixing the plurality of materials. A constituent material for the protective layer 7 is, for example, an organic material, such as a resin, or an inorganic material, such as silicon nitride, silicon oxide, or aluminum oxide. The layer can be formed by, for example, sputtering or an atomic layer deposition method (ALD method). Silicon nitride is also described as SiNx and silicon oxide is also as described as SiOx. X is a numerical value representing an element ratio.

A planarization layer may be arranged on the protective layer 7. The layer is arranged for preventing the wavelength-selecting portion 8 from being affected by the surface state of the protective layer 7. The planarization layer can be formed by, for example, a known production method, application method, or vacuum deposition method. The layer may be produced by performing, for example, CMP as required. A constituent material for the planarization layer is, for example, an organic material, such as a resin, or an inorganic material, such as SiNx, SiOx, or $Al_2O_3$, and may include an organic compound or a mixture of such material and compound. Examples of a formation method for the layer may include the same methods as those for the protective layer 7.

(8) Wavelength-Selecting Portion 8

The wavelength-selecting portion 8 is arranged on the planarization layer. When the photoelectric conversion element does not include the planarization layer, the portion is arranged on the protective layer 7. The wavelength-selecting portion 8 can be arranged on the light incident side of the photoelectric conversion element. Examples of the wavelength-selecting portion 8 include a color filter, a scintillator, and a prism. The color filter is a filter configured to transmit light having a predetermined wavelength in a quantity larger than that of light having any other wavelength. For example, the element can correspond to the entirety of the visible light region by using three kinds of color filters, that is, R, G, and B color filters. When the three kinds of color filters, that is, the R, G, and B color filters are used, a Bayer array, a delta array, or the like may be used as the arrangement of the color filters. In addition, the wavelength-selecting portion may be a prism configured to separate only light having a predetermined wavelength. The position at which the wavelength-selecting portion 8 is arranged is not limited to the position illustrated in FIG. 2. The wavelength-selecting portion 8 only needs to be arranged at any position on an optical path from an object or a light source to the photoelectric conversion layer 1.

(9) Microlens 9

The microlens 9 is an optical member for converging light from the outside in the first organic layer 1. Although a hemispherical lens is illustrated in FIG. 2, the shape of the microlens is not limited thereto. The microlens 9 includes, for example, quartz, silicon, or an organic resin. The shape and material of the microlens are not limited as long as its light convergence is not inhibited.

(10) Other Construction

The photoelectric conversion element may include any other photoelectric conversion element on an electrode. When the other photoelectric conversion element is a photoelectric conversion element configured to perform the photoelectric conversion of light having a wavelength different from that of light to be subjected to photoelectric conversion by the foregoing element, the light having the different wavelength can be detected at an identical or substantially identical in-plane position on the substrate.

In addition, the photoelectric conversion element may be constructed as follows: the element further includes another kind of organic compound layer configured to perform the photoelectric conversion of light having a wavelength different from that of light to be subjected to photoelectric conversion by the first organic layer 1, and the first organic layer 1 and the other kind of organic compound layer are laminated. With the construction, as in the construction in which the photoelectric conversion elements are laminated, the light having the different wavelength can be detected at an identical position or a substantially identical position on the substrate.

[Imaging Device According to Embodiment of the Present Disclosure and Imaging Apparatus Including the Device]

(1) Imaging Device

The photoelectric conversion element according to the embodiment of the present disclosure can be used in an imaging device. The imaging device includes: a plurality of photoelectric conversion elements serving as light-receiving pixels; a readout circuit connected to each of the photoelectric conversion elements; and a signal processing circuit (signal processing portion) connected to the readout circuit. Information based on charge that has been read out is transmitted to the signal processing portion connected to the imaging device. Examples of the signal processing portion include a CMOS sensor and a CCD sensor. When pieces of information acquired in the respective light-receiving pixels are gathered in the signal processing portion, an image can be obtained.

The imaging device may include a plurality of photoelectric conversion elements, and the plurality of photoelectric conversion elements may have color filters different from each other in kind. The plurality of kinds of color filters are color filters configured to transmit light beams having wavelengths different from each other. Specifically, the elements may have the respective R, G, and B color filters. The plurality of photoelectric conversion elements may include a photoelectric conversion layer as a common layer. The term "common layer" means that the photoelectric conversion layer of a photoelectric conversion element and the photoelectric conversion layer of a photoelectric conversion element adjacent thereto are one and the same.

Figure 3:
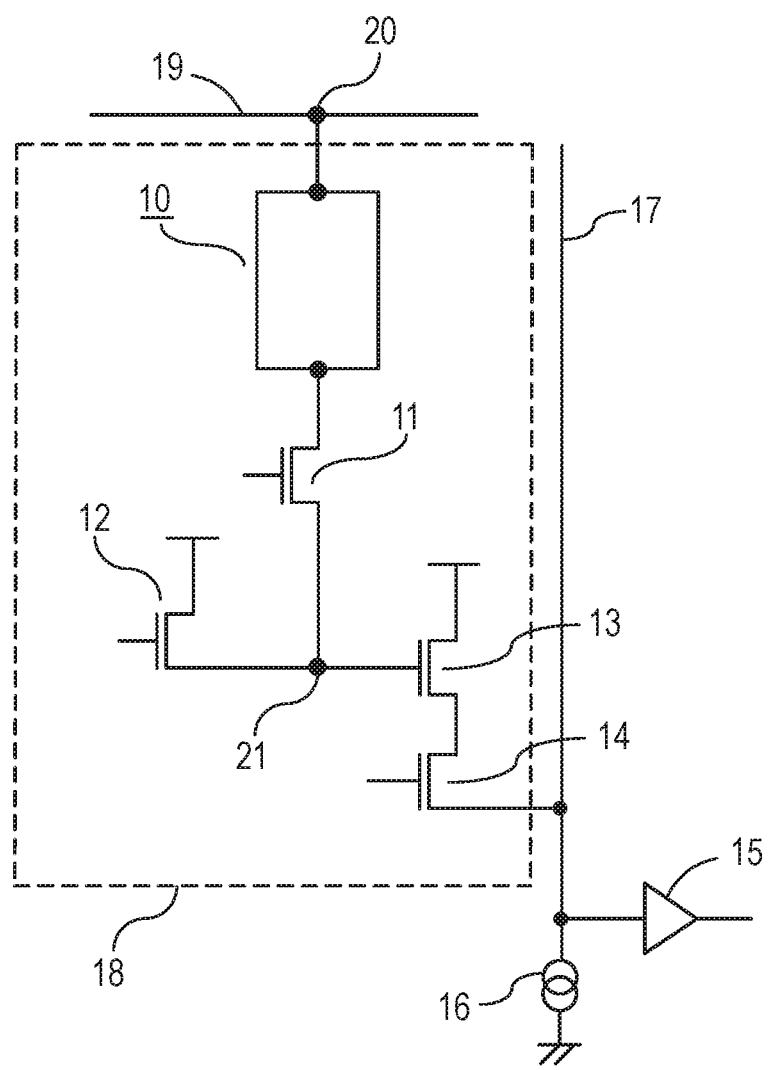
FIG. 3 is a circuit diagram of a pixel including the photoelectric conversion element according to the embodiment of the present disclosure.

FIG. 3 is a circuit diagram of a pixel including the photoelectric conversion element according to the embodiment of the present disclosure. The photoelectric conversion element 10 is connected to a common wiring 19 by a node A 20. The common wiring 19 may be connected to the ground. A pixel 18 may include the photoelectric conversion element 10 and a readout circuit for reading out a signal produced in the photoelectric conversion portion. The readout circuit may include, for example, a transfer transistor 11 electrically connected to the photoelectric conversion element 10, an amplification transistor 13 having a gate electrode electrically connected to the photoelectric conversion element 10, a selection transistor 14 configured to select a pixel from which information is read out, and a reset transistor 12 configured to supply a reset voltage to the photoelectric conversion element 10.

Transfer by the transfer transistor 11 may be controlled by a gate voltage. The supply of the reset voltage by the reset transistor 12 may be controlled by a voltage to be applied to its gate. The selection transistor 14 is brought into a selection or non-selection state by its gate voltage. The transfer transistor 11, the reset transistor 12, and the amplification transistor 13 are connected to one another by a node B 21. The readout circuit may be free of the transfer transistor 11 depending on its construction. The reset transistor 12 is a transistor configured to supply a voltage configured to reset the potential of the node B 21. The application of a signal to the gate of the reset transistor 12 can control the supply of the voltage. The circuit may be free of the reset transistor 12 depending on the construction. The amplification transistor 13 is a transistor configured to flow a current in accordance with the potential of the node B 21. The amplification transistor 13 is connected to the selection transistor 14 configured to select the pixel 18 from which a signal is output. The selection transistor 14 is connected to a current source 16 and a column output portion 15, and the column output portion 15 is connected to the signal processing portion. The selection transistor 14 is connected to a vertical output signal line 17. The vertical output signal line 17 is connected to the current source 16 and the column output portion 15.

Figure 4:
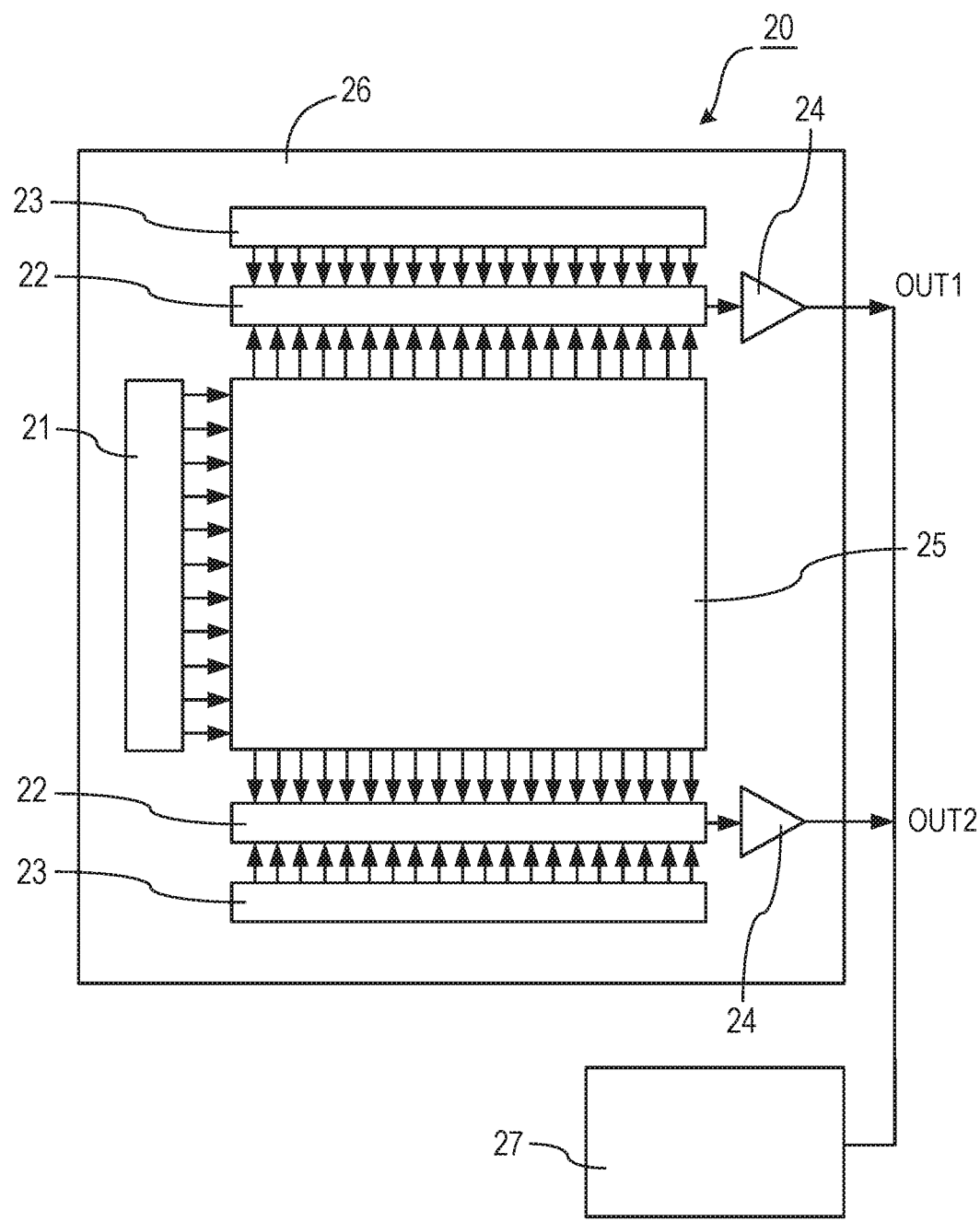
FIG. 4 is a schematic view for illustrating an imaging device according to an embodiment of the present disclosure.

FIG. 4 is a schematic view for illustrating the imaging device according to an embodiment of the present disclosure. An imaging device 20 includes an image pickup region 25 in which a plurality of pixels are arranged in a two-dimensional manner, and a peripheral region 26. The region except the image pickup region 25 is the peripheral region 26. The peripheral region 26 has a vertical scanning circuit 21, readout circuits 22, horizontal scanning circuits 23, and output amplifiers 24, and the output amplifiers 24 are connected to a signal processing portion 27. The signal processing portion 27 is a signal processing portion configured to perform signal processing based on information read out in the readout circuits 22, and examples thereof include a CCD circuit and a CMOS circuit.

Each of the readout circuits 22 includes, for example, a column amplifier, a correlated double sampling (CDS) circuit, and an addition circuit, and performs the amplification, addition, and the like of a signal read out from a pixel in a row selected by the vertical scanning circuit 21 through a vertical signal line. The column amplifier, the CDS circuit, the addition circuit, and the like are arranged in, for example, each pixel column or each plurality of pixel columns. The CDS circuit is a circuit configured to perform CDS signal processing, and performs a kTC noise reduction.

The horizontal scanning circuits 23 produce signals for reading out the signals of the readout circuits 22 in order. The output amplifiers 24 amplify and output the signals of columns selected by the horizontal scanning circuits 23.

The foregoing construction is merely a construction example of the imaging device, and the embodiment of the present disclosure is not limited thereto. The readout circuits 22, the horizontal scanning circuits 23, and the output amplifiers 24 are vertically arranged one by one across the image pickup region 25 in order that two output paths may be formed. However, three or more output paths may be arranged. Signals output from the respective output amplifiers 24 are synthesized as an image signal in the signal processing portion 27.

(2) Imaging Apparatus

The imaging device according to the embodiment of the present disclosure can be used in an imaging apparatus. The imaging apparatus includes an imaging optical system having a plurality of lenses, and an imaging device configured to receive light that has passed the imaging optical system. In addition, the imaging apparatus includes an imaging device and a casing configured to store the imaging device, and the casing may have a joining portion capable of being joined to an imaging optical system. The imaging apparatus is more specifically a digital camera or a digital still camera.

In addition, the imaging apparatus may include a communicating portion configured to allow an image that has been picked up to be viewed from the outside. The communicating portion may include a receiving portion configured to receive a signal from the outside or a transmitting portion configured to transmit information to the outside. The signal received by the receiving portion is a signal configured to control at least one of the image pickup range of the imaging apparatus, the start of the image pickup thereof, or the end of the image pickup. In addition, the transmitting portion may transmit, in addition to the image that has been picked up, information, such as a warning about the image, the remaining amount of a data capacity, and the remaining amount of a power source. When the apparatus includes the receiving portion or the transmitting portion, the apparatus can be used as a network camera.

EXAMPLES

The present disclosure is described in detail below by way of Examples. The present disclosure is not limited to these Examples.

Example 1

(Synthesis of Exemplified Compound A-1)

Exemplified Compound A-1 was synthesized by the following scheme.

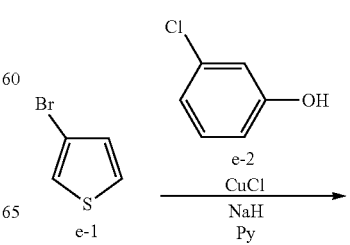

-continued

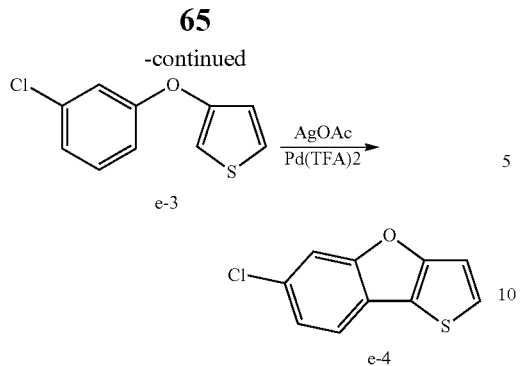

4.89 Grams (30.0 mmol) of e-1, 3.85 g (30.0 mmol) of e-2, and 60 ml of pyridine were loaded into a 200-milliliter flask. Further, 0.99 g (20.0 mmol) of copper(I) chloride and 1.20 g (20.0 mmol) of 60% sodium hydride were added to the mixture, and the whole was heated to a temperature of 120° C. and stirred for 6 hours. The resultant was cooled, and was then extracted with toluene and concentrated. The residue was purified by silica gel column chromatography (mobile phase; mixed solvent of heptane and toluene) to provide 1.20 g of a white solid e-3 (yield: 19%).

1.20 Grams (5.70 mmol) of e-3 and 10 ml of propionic acid were loaded into a 50-milliliter flask. Further, 0.190 g of palladium bistrifluoracetate and 1.90 g (11.4 mmol) of silver acetate were added to the mixture, and the whole was heated to a temperature of 110° C. and stirred for 5 hours. The resultant was cooled, and was then extracted with toluene and concentrated. The residue was purified by silica gel column chromatography (mobile phase; mixed solvent of heptane and toluene) to provide 0.735 g of a white solid e-4 (yield: 62%).

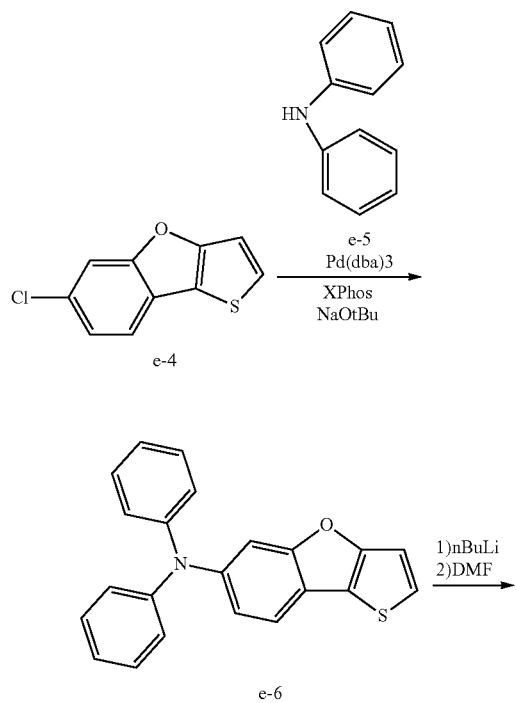

-continued

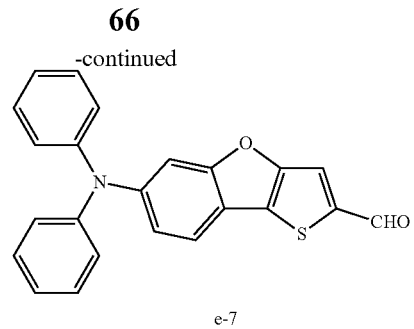

183 Milligrams (0.2 mmol) of Pd(dba)₃ and 286 mg (0.6 mmol) of Xphos were loaded into 5 ml of toluene, and the mixture was stirred at room temperature for 15 minutes. The solution was added to a separately prepared solution of 0.730 g (3.51 mmol) of e-4 and 0.652 g (3.86 mmol) of e-5 in 15 ml of toluene. Further, 0.672 g (7.2 mmol) of sodium tert-butoxide was added to the mixture, and the whole was stirred at 120° C. for 4 hours. The resultant was cooled, and was then filtered with Celite and concentrated. The residue was purified by silica gel column chromatography (mobile phase; mixed solvent of heptane and toluene) to provide 0.738 g of a whitish yellow solid e-6 (yield: 62%).

0.492 Gram (1.43 mmol) of e-6 was loaded into 15 ml of tetrahydrofuran, and the mixture was cooled to −78° C. Further, 1.06 ml (1.73 mmol) of n-butyllithium (1.6 M n-hexane solution) was dropped into the mixture at −78° C. After the dropping, the temperature of the reaction solution was increased to −40° C., and the solution was stirred for 2 hours. Further, 2.86 ml (2.86 mmol) of DMF was dropped into the solution at −40° C., and the mixture was stirred for 3 hours while its temperature was slowly increased to room temperature. After the reaction, an aqueous solution of ammonium chloride was added to the resultant, and the mixture was extracted with ethyl acetate. The extract was concentrated, and then the residue was purified by silica gel column chromatography (mobile phase; mixed layer of heptane and chloroform) to provide 0.389 g of a yellow solid e-7 (yield: 74%).

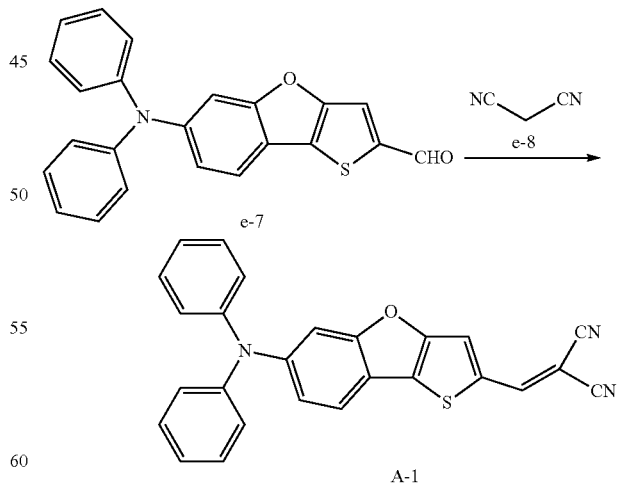

0.350 Milligram (0.972 mmol) of e-7 was loaded into 10 ml of chloroform. Further, 0.083 mg (1.26 mmol) of e-8 and 3 droplets of triethylamine were added to the mixture, and the whole was stirred as it was for 2 hours. After the reaction, the resultant was extracted with chloroform and concentrated. After that, the residue was purified by silica gel column chromatography (mobile phase; chloroform) to provide 0.350 g of a dark red solid A-1 (yield: 85%). Mass spectrometry identified a peak at an m/z of 417 corresponding to the M$^+$ of Exemplified Compound A-1.

Example 2

(Synthesis of Exemplified Compound B-1)

Exemplified Compound B-1 was similarly synthesized by using e-7 of Example 1 as an intermediate.

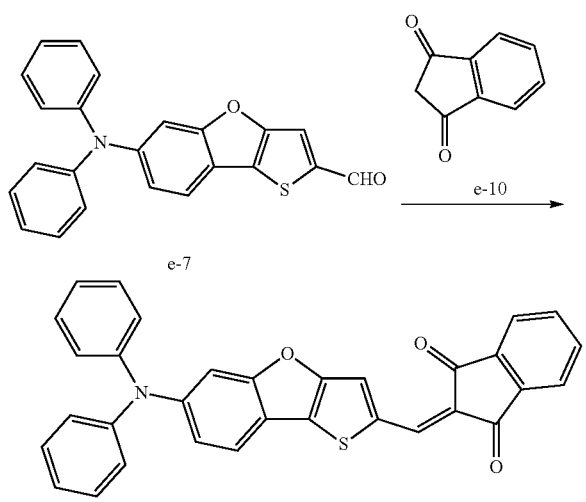

0.359 Milligram (0.972 mmol) of the intermediate e-7 was loaded into 10 ml of chloroform. Further, 0.184 mg (1.26 mmol) of e-10 and 3 droplets of piperidine were added to the mixture, and the whole was stirred as it was for 4 hours. After the reaction, the resultant was extracted with chloroform and concentrated. After that, the residue was purified by silica gel column chromatography (mobile phase; chloroform) to provide 0.351 g of a dark red solid B-1 (yield: 73%). Mass spectrometry identified a peak at an m/z of 497 corresponding to the M$^+$ of Exemplified Compound B-1.

The absorption spectrum of Exemplified Compound B-1 in a chloroform dilute solution ($3 \times 10^{-5}$ mol/L) was measured. As a result, as shown in FIG. 1, the maximum absorption wavelength in a visible light region was 558 nm. Further, the molar extinction coefficient of the compound in the chloroform dilute solution ($3 \times 10^{-5}$ mol/L) was measured. As a result, the molar extinction coefficient was 63,400 M$^{-1}$ cm$^{-1}$ at a wavelength of 558 nm. A UV-visible spectrophotometer V-560 manufactured by JASCO Corporation was used as an apparatus.

Examples 3 to 13

Exemplified compounds shown in Tables 6 and 7 were each synthesized in the same manner as in Examples 1 and 2 except that: e-5 was changed to a diarylamino raw material shown in Table 6 or 7; and e-8 or e-10 was changed to an electron-withdrawing group raw material shown in Table 6 or 7. In addition, the M$^+$ of each of the exemplified compounds was identified by mass spectrometry.

TABLE 6

| Example | Diarylamino raw material | Electron-withdrawing group raw material | Exemplified Compound No. | M$^+$ identified by mass spectrometry |
|---|---|---|---|---|
| Example 3 | ![structure] | NC–CN | A-2 | 446 |
| Example 4 | ![structure] | NC–CN | A-4 | 474 |

TABLE 6-continued

| Example | Diarylamino raw material | Electron-withdrawing group raw material | Exemplified Compound No. | M+ identified by mass spectrometry |
|---|---|---|---|---|
| Example 5 | (3,4,5-trimethylphenyl)(naphthalen-2-yl)amine | NC-CH2-CN | A-5 | 510 |
| Example 6 | bis(4-tert-butylphenyl)amine | NC-CH2-CN | A-6 | 530 |
| Example 7 | N-phenylquinolin-2-amine | NC-CH2-CN | A-7 | 469 |

TABLE 7

| Example | Diarylamino raw material | Electron-withdrawing group raw material | Exemplified Compound No. | M+ identified by mass spectrometry |
|---|---|---|---|---|
| Example 8 | bis(2,4,6-trifluorophenyl)amine | NC-CH2-CN | A-9 | 525 |

TABLE 7-continued
| Example | Diarylamino raw material | Electron-withdrawing group raw material | Exemplified Compound No. | M+ identified by mass spectrometry |
|---|---|---|---|---|
| Example 9 | 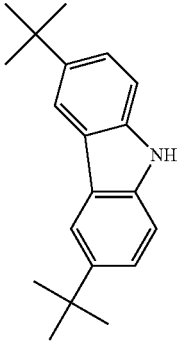 [SMILES: CC(C)(C)c1ccc2[nH]c3ccc(C(C)(C)C)cc3c2c1] | 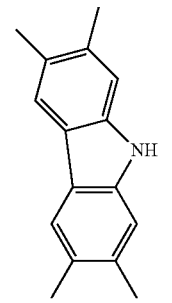 | A-13 | 528 |
| Example 10 | 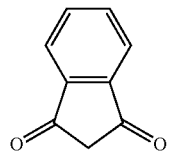 | 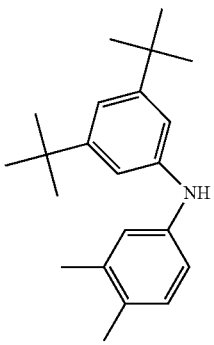 [SMILES: Cc1ccc(Nc2cc(C(C)(C)C)cc(C(C)(C)C)c2)cc1C] | B-2 | 554 |
| Example 11 | 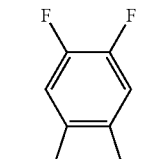 | 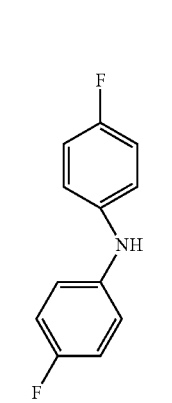 | B-3 | 674 |
| Example 12 | 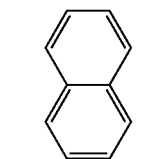 | | B-9 | 584 |

TABLE 7-continued

| Example | Diarylamino raw material | Electron-withdrawing group raw material | Exemplified Compound No. | M+ identified by mass spectrometry |
|---|---|---|---|---|
| Example 13 | (structure) | (structure) | B-12 | 527 |

Example 14

A photoelectric conversion element in which the hole-collecting electrode (cathode) 4, the electron-blocking layer (second organic layer) 2, the photoelectric conversion layer (first organic layer) 1, the hole-blocking layer (third organic layer) 3, and the electron-collecting electrode (anode) 5 were sequentially formed on a substrate was produced. First, an IZO film was formed on a Si substrate and subjected to desired patterning processing to form an IZO electrode (the hole-collecting electrode 4). At this time, the thickness of the IZO electrode was set to 100 nm. The substrate on which the IZO electrode had been formed as described above was used as an IZO substrate in the following process. Organic compound layers (the second organic layer 2, the first organic layer 1, and the third organic layer 3) and an electrode layer (the electron-collecting electrode 5) shown in Table 8 were continuously formed on the IZO substrate. At this time, the electrode area of the opposing electrode (the electron-collecting electrode 5) was set to 3 mm².

TABLE 8

| | Constituent material | Thickness [nm] |
|---|---|---|
| Electron-collecting electrode | IZO | 30 nm |
| Third organic layer | g-3 (C60) | 50 nm |
| First organic layer | Exemplified Compound A-1:g-3 (C60) = 25:75 [mass ratio] | 400 nm |
| Second organic layer | g-1 | 100 nm |
| Hole-collecting electrode | IZO | 100 nm |

Materials g-1 and g-3 used in this Example, and Material g-2 to be used in Examples 21 and 22 to be described later are as shown below.

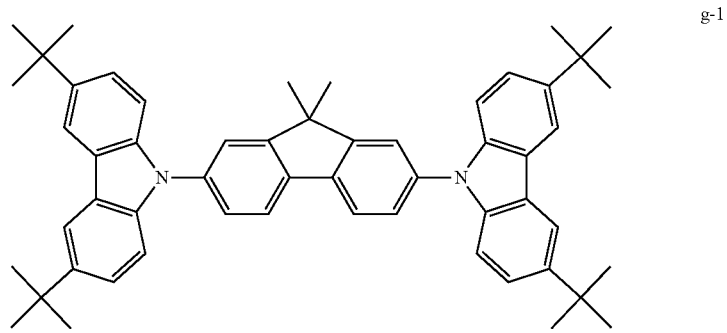

g-1

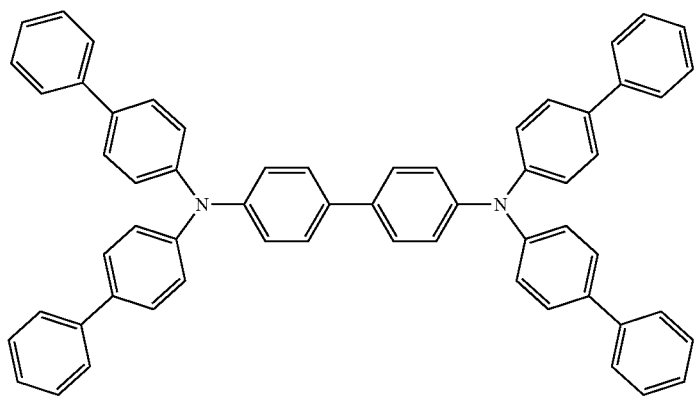

g-2

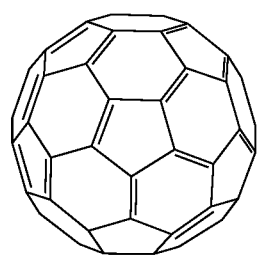

g-3

Examples 15 to 22, and Comparative Examples 1 and 2

Photoelectric conversion elements were each obtained by the same method as that of Example 14 except that the electron donor material (Exemplified Compound A-1) in the first organic layer 1 and the second organic layer 2 (g-1) were changed as shown in Table 9.

TABLE 9

| | Electron donor material | Second organic layer | External quantum efficiency |
|---|---|---|---|
| Example 15 | A-2 | g-1 | A |
| Example 16 | A-3 | g-1 | A |

TABLE 9-continued

| | Electron donor material | Second organic layer | External quantum efficiency |
|---|---|---|---|
| Example 17 | A-5 | g-1 | A |
| Example 18 | A-6 | g-1 | B |
| Example 19 | A-9 | g-1 | B |
| Example 20 | B-2 | g-1 | A |
| Example 21 | B-3 | g-2 | A |
| Example 22 | A-2 | g-2 | B |
| Comparative Example 1 | a-1 | g-1 | C |
| Comparative Example 2 | b-1 | g-1 | Unable to produce element owing to decomposition |

Compounds a-1 and b-1 used in Comparative Examples 1 and 2 are as shown below.

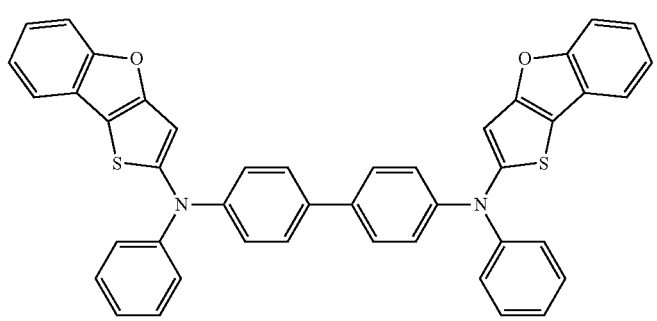

a-1

-continued b-1

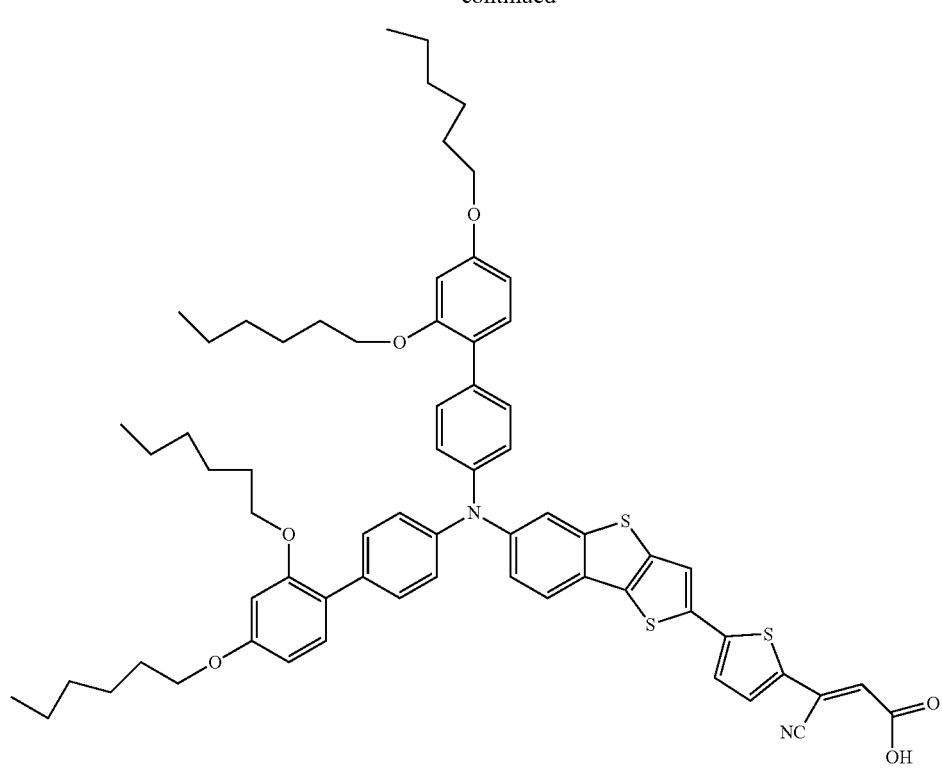

[Evaluation of Photoelectric Conversion Element]

A voltage of 5 V was applied to each of the resultant elements, and external quantum efficiency at that time was measured. The external quantum efficiency was calculated by measuring the density of a photocurrent flowing when the element was irradiated with monochromatic light having an intensity of 50 µW/cm$^2$, the light corresponding to each wavelength, under a state in which the voltage of 5 V was applied between the hole-collecting electrode 4 and the electron-collecting electrode 5. Here, the photocurrent density was determined by subtracting the density of a dark current at the time of light shielding from a current density at the time of the light irradiation. The monochromatic light used at the time of the measurement of the photocurrent density is obtained by monochromatizing white light output from a xenon lamp (apparatus name: XB-50101AA-A, manufactured by Ushio Inc.) with a monochromator (apparatus name: MC-10N, manufactured by Ritu Oyo Kougaku Co., Ltd.). The application of the voltage to the element and the current measurement were performed with a source meter (apparatus name: R6243, manufactured by Advantest Corporation). In addition, the light was caused to enter vertically to the element and from an upper electrode (electron-collecting electrode 5) side.

A relative value for external quantum efficiency at a wavelength of 600 nm when the external quantum efficiency of the photoelectric conversion element of Example 14 was defined as 1 was evaluated by the following criteria. The results are shown in Table 9.

A: A case in which the relative value for the external quantum efficiency is 0.9 or more
B: A case in which the relative value for the external quantum efficiency is 0.7 or more and less than 0.9
C: A case in which the relative value for the external quantum efficiency is less than 0.5

It was found from the results shown in Table 9 that an element was able to be produced from the compound according to the embodiment of the present disclosure without its decomposition at the time of vapor deposition, and the produced photoelectric conversion element had sensitivity at wavelengths longer than 600 nm in the visible light region.

According to the present disclosure, there can be provided an organic compound that has light absorption in a wide range of a visible light region and is excellent in thermal stability.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-152269, filed Aug. 7, 2017, which is hereby incorporated by reference herein in its entirety.

What is claimed is:

1. An organic compound, which is represented by general formula [1]:

[1]

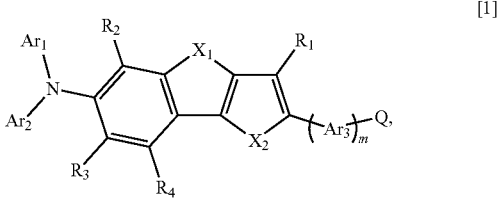

wherein $Ar_1$ and $Ar_2$ are each independently selected from the group consisting of an aryl group and a heteroaryl group, the $Ar_1$ and the $Ar_2$ may each have a halogen atom, a cyano group, an alkyl group, an alkoxy group, an aryl group, or a heteroaryl group as a substituent, the substituent may further have a halogen atom, a cyano group, an alkyl group, or an alkoxy group as a substituent, the $Ar_1$ and the $Ar_2$ may be bonded to each other to form a ring, $Ar_3$ is selected from the group consisting of an arylene group and a heteroarylene group, and m represents an integer of 0 to 3, and when the m represents 2 or 3, a plurality of the $Ar_3$ may be identical to or different from each other, $R_1$ to $R_4$ are each independently selected from the group consisting of a hydrogen atom, a halogen atom, a cyano group, an alkyl group, an alkoxy group, an aryl group, and a heteroaryl group, the alkyl group represented by any one of the $R_1$ to the $R_4$ may have a halogen atom as a substituent, and the aryl group and the heteroaryl group each represented by any one of the $R_1$ to the $R_4$ may each further have a halogen atom, a cyano group, an alkyl group, or an alkoxy group as a substituent, $X_1$ and $X_2$ are each independently selected from oxygen and sulfur, and Q represents a substituent selected from the group consisting of general formulae [1-1] and [1-2]:

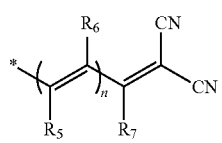

[1-1]

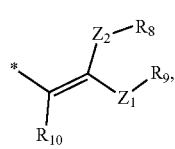

[1-2]

wherein, in the general formulae [1-1] and [1-2], * represents a bonding position, $R_5$ to $R_{10}$ are each independently selected from the group consisting of a hydrogen atom, a halogen atom, a cyano group, an amino group, an amide group, an alkyl group, an alkoxy group, an alkenyl group, an alkynyl group, an aryl group, and a heteroaryl group, and the $R_7$ and the $R_5$ adjacent to the $R_7$ may be bonded to each other to form a ring, and the $R_8$ and the $R_9$ may be bonded to each other to form a ring, and the $R_5$ to the $R_{10}$ may each have a halogen atom, a cyano group, an alkyl group, an alkoxy group, an aryl group, or a heteroaryl group as a substituent, wherein, in the general formula [1-1], n represents an integer of 0 to 2, and wherein, in the general formula [1-2], $Z_1$ and $Z_2$ are each independently selected from the group consisting of formulae [1-3] to [1-5]:

[1-3]

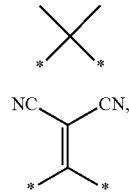

[1-4]

[1-5]

wherein, in the formulae [1-3] to [1-5], * represents a bonding position.

2. The organic compound according to claim 1, wherein the $X_1$ represents oxygen and the $X_2$ represents sulfur.

3. The organic compound according to claim 1, wherein the m represents 0.

4. An organic compound represented by general formula [2]:

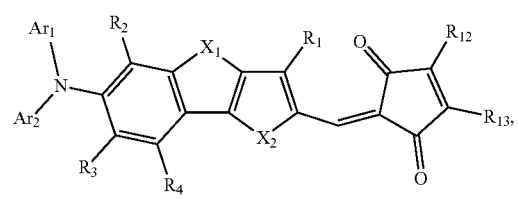

[2]

wherein $Ar_1$ and $Ar_2$ are each independently selected from the group consisting of an aryl group and a heteroaryl group, the $Ar_1$ and the $Ar_2$ may each have a halogen atom, a cyano group, an alkyl group, an alkoxy group, an aryl group, or a heteroaryl group as a substituent, the substituent may further have a halogen atom, a cyano group, an alkyl group, or an alkoxy group as a substituent, the $Ar_1$ and the $Ar_2$ may be bonded to each other to form a ring, wherein $R_1$ to $R_4$ are each independently selected from the group consisting of a hydrogen atom, a halogen atom, a cyano group, an alkyl group, an alkoxy group, an aryl group, and a heteroaryl group, the alkyl group represented by any one of the $R_1$ to the $R_4$ may have a halogen atom as a substituent, and the aryl group and the heteroaryl group each represented by any one of the $R_1$ to the $R_4$ may each further have a halogen atom, a cyano group, an alkyl group, or an alkoxy group as a substituent, wherein $X_1$ and $X_2$ are each independently selected from oxygen and sulfur, and wherein $R_{12}$ and $R_{13}$ are each independently selected from the group consisting of a halogen atom, a cyano group, an amino group, an amide group, an alkyl group, an alkoxy group, an alkenyl group, an alkynyl group, an aryl group, and a heteroaryl group, and the $R_{12}$ and the $R_{13}$ may each have a halogen atom, a cyano group, an alkyl group, an alkoxy group, an aryl group, or a heteroaryl group as a substituent, and the $R_{12}$ and the $R_{13}$ may be bonded to each other to form a ring.

5. The organic compound according to claim 4, wherein the ring formed by the bonding of the $R_{12}$ and the $R_{13}$ to each other comprises one of a benzene ring, a naphthalene ring, a pyridine ring, a pyrimidine ring, a pyrazine ring, a pyridazine ring, a quinoline ring, an isoquinoline ring, a quinoxaline ring, a thiophene ring, a benzothiophene ring, a furan ring, and a benzofuran ring.

6. The organic compound according to claim 1, wherein the organic compound is represented by general formula [3]:

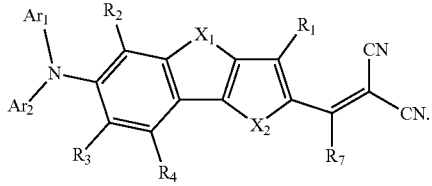 [3]

7. A photoelectric conversion element comprising:
an anode;
a cathode; and
an organic compound layer arranged between the anode and the cathode,
wherein the organic compound layer has a first organic layer containing the organic compound of claim 1.

8. The photoelectric conversion element according to claim 7, wherein the first organic layer comprises a photoelectric conversion layer and contains an organic n-type compound.

9. The photoelectric conversion element according to claim 8, wherein the organic n-type compound comprises one of a fullerene and a fullerene derivative.

10. An imaging device comprising:
the photoelectric conversion element of claim 7;
a readout circuit connected to the photoelectric conversion element; and
a signal processing circuit connected to the readout circuit.

11. An imaging apparatus comprising:
an imaging optical system; and
an imaging device configured to receive light that has passed the imaging optical system,
wherein the imaging device comprises the imaging device of claim 10.

12. An imaging apparatus comprising:
the imaging device of claim 10; and
a casing configured to store the imaging device,
wherein the casing has a joining portion capable of being joined to an imaging optical system.

13. The imaging apparatus according to claim 11, further comprising a receiving portion configured to receive a signal from an outside, wherein the signal comprises a signal configured to control at least one of an imaging range of the imaging apparatus, a start of imaging thereof, or an end of the imaging.

14. The imaging apparatus according to claim 11, further comprising a transmitting portion configured to transmit an acquired image to an outside.

* * * * *